(12) United States Patent
Forman et al.

(10) Patent No.: US 8,771,310 B2
(45) Date of Patent: Jul. 8, 2014

(54) ANTI-NO-REFLOW GUIDE WIRE FOR VASCULAR INTERVENTIONAL PROCEDURES

(75) Inventors: Mervyn B. Forman, Atlanta, GA (US); Edwin K. Jackson, Pittsburgh, PA (US); Jianying Zhang, Pittsburgh, PA (US); Zaichuan Mi, Wexford, PA (US)

(73) Assignee: Adenopaint, LLC, Atlanta, GA (US)

( * ) Notice: Subject to any disclaimer, the term of this patent is extended or adjusted under 35 U.S.C. 154(b) by 870 days.

(21) Appl. No.: 12/514,189

(22) PCT Filed: May 28, 2008

(86) PCT No.: PCT/US2008/064997
§ 371 (c)(1),
(2), (4) Date: Oct. 14, 2009

(87) PCT Pub. No.: WO2008/150807
PCT Pub. Date: Dec. 11, 2008

(65) Prior Publication Data
US 2010/0036411 A1  Feb. 11, 2010

Related U.S. Application Data

(60) Provisional application No. 60/941,062, filed on May 31, 2007.

(51) Int. Cl.
*A61M 29/00* (2006.01)

(52) U.S. Cl.
USPC ............... 606/194; 527/300; 536/27.6

(58) Field of Classification Search
None
See application file for complete search history.

(56) References Cited

U.S. PATENT DOCUMENTS

| | | | |
|---|---|---|---|
| 2005/0220853 A1* | 10/2005 | Dao et al. | 424/449 |
| 2006/0216323 A1* | 9/2006 | Knaack et al. | 424/422 |
| 2007/0141107 A1 | 6/2007 | Kutryk et al. | |
| 2007/0224240 A1 | 9/2007 | Toner et al. | |

FOREIGN PATENT DOCUMENTS

| | | | |
|---|---|---|---|
| JP | 19860232832 | * | 9/1986 |
| WO | 03/035132 | * | 5/2003 |
| WO | WO 03/035132 A1 | | 5/2003 |

OTHER PUBLICATIONS

Fischell et al ("Reversal of "No Reflow" During Vein Graft Stenting Using High Velocity Boluses of Intracoronary Adenosine," Catheterization and Cardiovascular Diagnosis 45:360-365 (1998).*
Database WPI Week 198821 Thomson Scientific, London, GB; AN, 1988-143415 XP002543396 & JP 63 084556 A (Unitika Ltd) Apr. 15, 1988.

* cited by examiner

*Primary Examiner* — Suzanne Ziska
(74) *Attorney, Agent, or Firm* — Ballard Spahr LLP

(57) ABSTRACT

The present invention relates to compositions and methods for improving outcomes in vascular interventional procedures. In particular, the present invention relates to compositions and methods for improving outcomes in vascular interventional procedures using an anti-no-reflow guide wire that attenuates the "no-reflow" phenomenon that is associated with negative outcomes.

21 Claims, 22 Drawing Sheets

FT-IR spectrum of the prepolymer made by 0.26g adenosine-0.85g LDI-in 2 ml DMSO-2 days-0.8g adenosine-0.185g cysteine ethyl ester-5 ml DMSO Anode (+) reaction: $2R\text{-}SH - 2e^- \longrightarrow R\text{-}S\text{-}S\text{-}R + 2H^+$ Cathode (-) reaction: $R\text{-}S\text{-}S\text{-}R + 2e^- + 2H^+ \longrightarrow 2R\text{-}SH$

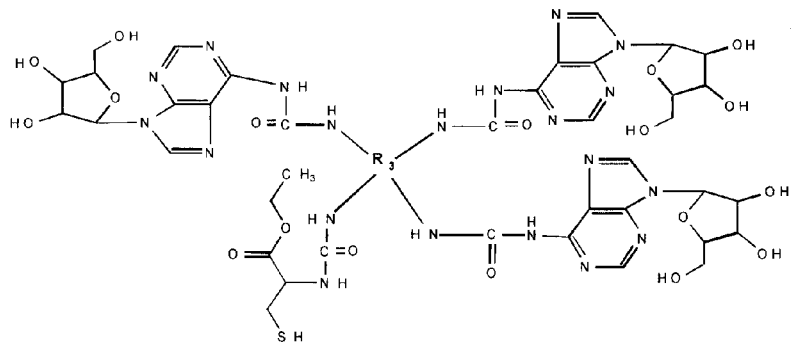
(Adenosine-LDI-Cysteine monomer)
$-2H^+; -2e$
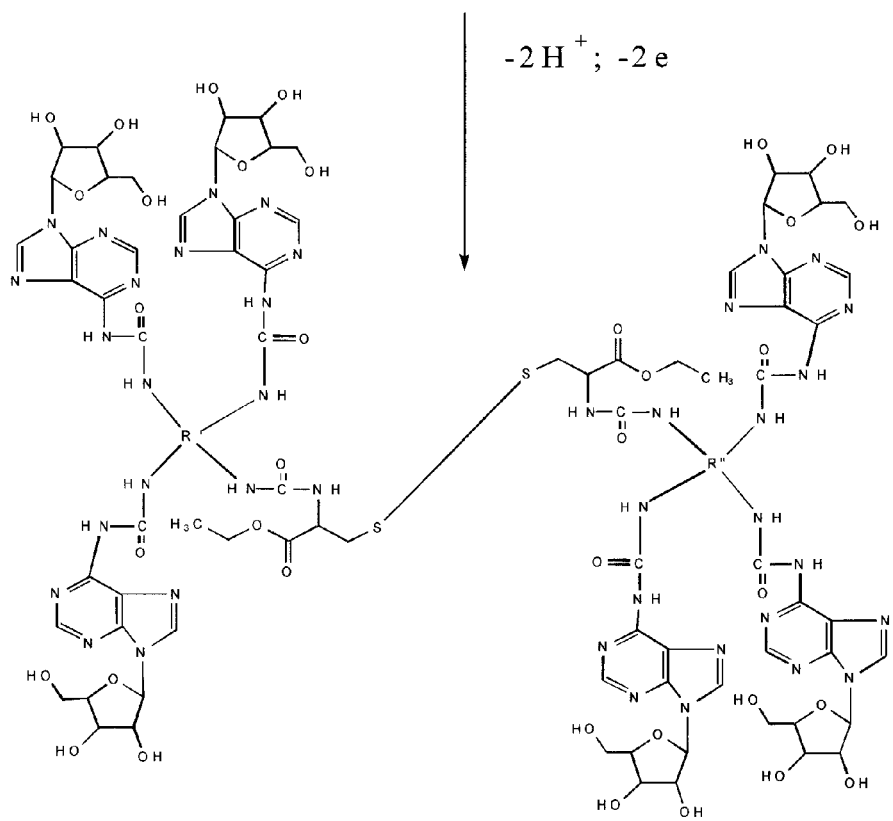
Figure 15

Figure 20
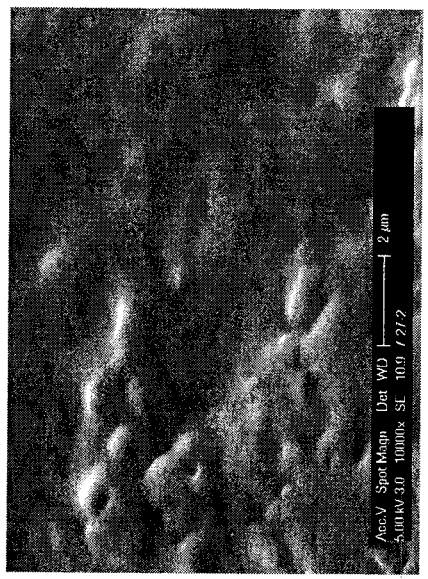
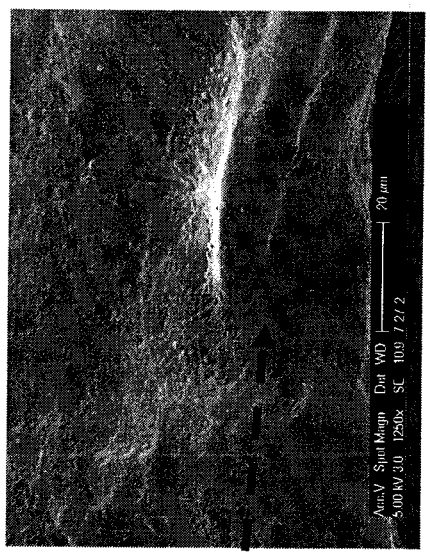
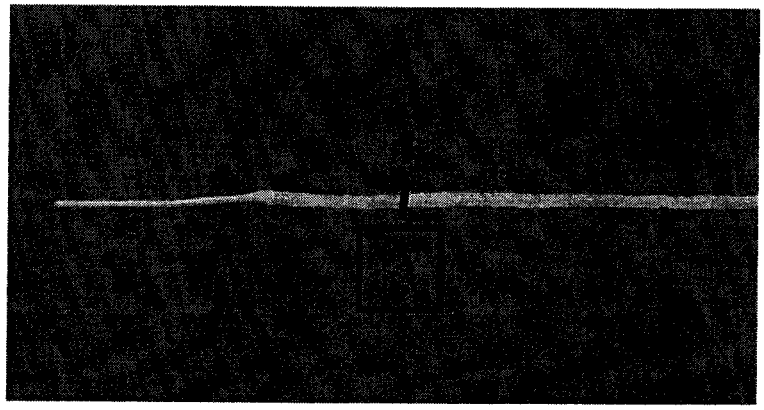
Magnification = 10,000X
Magnification = 1250X

ANTI-NO-REFLOW GUIDE WIRE FOR VASCULAR INTERVENTIONAL PROCEDURES

CROSS REFERENCE TO RELATED APPLICATIONS

The present application is a National Phase Application of International Application No. PCT/US2008/064997, filed May 28, 2008, which claims priority to U.S. Provisional Patent Application No. 60/941,062 filed May 31, 2007, which applications are incorporated herein fully by this reference.

FIELD OF THE INVENTION

The present invention relates to compositions and methods for improving outcomes in vascular interventional procedures. In particular, the present invention relates to compositions and methods for improving outcomes in vascular interventional procedures using a guide wire (for example an anti-no-reflow guide wire) that attenuates the "no-reflow" phenomenon that is associated with negative outcomes.

BACKGROUND

Atherosclerotic vascular disease remains a major cause of morbidity and mortality in spite of numerous advances in pharmacological modalities to modify associated risk factors. Atherosclerotic involvement of the myocardium, brain and kidneys is responsible for the majority of adverse affects of the disorder. Coronary artery disease remains the leading cause of death in the Westernized world. Approximately 1.5 million Americans per year suffer a myocardial infarction with an annual death toll of 400,000 (see e.g., Thom, T., et al., Circulation 113: 85 (2006)). Cerebrovascular disease is the third leading cause of death with stenosis of the internal carotid artery accounting for 20% of strokes and transient ischemic attacks (TIAs) (see e.g., Heart Disease and Stroke Statistics—2006 Update Dallas, Tx; AHA, (2006); Roffie, M., and Yadav, J. S., Circulation 114: el (2006)). Renal artery stenosis due to atherosclerosis is relatively common (6-8%) in patients >65 years of age and often results in progressive renal failure, worsening hypertension and precipitation of congestive heart failure and unstable angina (see e.g., Hansen, K. J., et al., J. Vasc. Surg. 36: 443 (2002); Pasternak, R. C., et al., Circulation 109: 2605 (2004)).

The rapid evolution of percutaneous balloon angioplasty (PTA) followed by the development of stent technology has resulted in increased utilization of vascular interventional procedures in the treatment of atherosclerotic-induced stenosis of the major blood vessels supplying the myocardium, brain, kidneys and peripheral vessels. Coronary artery stenting has surpassed coronary artery bypass surgery (CABG) as a treatment of choice to revascularize patients with a single or double vessel coronary artery disease with more than 700,000 procedures performed in the United States each year. Furthermore, stenting procedures are frequently performed in CABG patients who have degenerative and stenotic saphenous vein grafts (SVG) secondary to atherosclerosis.

In reference to the heart, patients with atherosclerosis may present with stable angina, acute coronary syndromes (ACS), namely unstable angina and non-ST segment elevation myocardial infarction (NSTEMI), or acute ST segment elevation infarction (STEMI). These syndromes occur in the setting of an unstable ulcerative plaque associated with a variable thrombus burden. These conditions can be successfully treated in the majority of patients with stent implantation resulting in restoration of normal vessel caliber. However, the introduction of a guide wire, balloon, stent or embolic protection device (EPD) may compromise tissue blood flow through macro-embolization of thrombotic and atherosclerotic debris into the distal vessel (see e.g., Topol, E. J., and Yadav, J. S., Circulation 101: 570 (2000)). This has been shown to occur in 14% of STEMI patients treated with percutaneous coronary intervention (PCI) and is associated with larger infarct size, worse left ventricular function and higher mortality (see e.g., Henriques, J. P., et al., Eur. Heart J. 23: 1112 (2002)). Embolization with atheromatous debris is even more frequent during PCI of SVG's (~80%) and results in increased mortality (see e.g., Trono, R., et al., Cleve. Clin. J. Med. 56:581 (1989)).

Vascular interventional procedures performed in the presence of an occlusive thrombus may also compromise tissue blood flow either through micro-embolization or via microvascular injury induced by the deterious effects of reperfusion (see e.g., Constantini, C. O., et al., J. Am. Coll. Cardiol. 44: 305 (2004); Kenner, M. D., et al., J. Am. Coll. Cardiol. 76: 861 (1995); van't H of A. W., et al., Circulation 97: 2302 (1998); Forman, M. B., et al., Cardiovascular Drug Reviews 24: 116 (2006)). The common occurrence of micro-embolization after interventional procedures has recently been appreciated by the frequent retrieval of atheroembolic material from EPDs. These particles consist of cellular and non-cellular elements with wide variations in size and volume (see e.g., Akbar O., et al., Am. Heart J. 152: 207 (2000)). Although the pathogenesis of reperfusion injury is complex and multi-factorial, the introduction of activated neutrophils and platelets associated with release of various vasoconstrictors produced from circulating cells and dysfunctional endothelial cells may contribute to a progressive decrease in flow during the peri-reperfusion period; defined as the "no-reflow" phenomenon (see e.g., Forman, M. B. et. al, Cardiovascular Drug Reviews 24: 116 (2006)). Impaired tissue perfusion occurs in 29-44% of reperfused patients, the highest incidence with occlusion of the left anterior descending coronary artery (50-80%), and correlates with infarct size, ventricular function and early and late mortality (see e.g., Bax, M., et al., J. Am. Coll. Cardiol. 43: 534 (2004); Ito, H., et al., Circulation 93: 1993 (1996); Deluca, G., et al., Circulation 109: 958 (2004); Wu, K. C., et al., Circulation 97: 765 (1998)). Furthermore, numerous studies have demonstrated that abnormal tissue perfusion, as assessed by myocardial blush grade (MBG), is an independent, multivariate predictor of both early and late mortality in STEMI undergoing thrombolysis or PCI. Abnormal MBG (0-1) results in a 7-fold increase in mortality which is maintained for up to 2 years (see e.g., Gibson, C. M. and Schömig, A., Circulation 109: 3096 (2004); Forman, M. B., and Jackson, E. K., Clin. Cardiol. 30: 583 (2007)). Abnormal tissue perfusion following PCI in patients with NSTEMI is also associated with higher risk of myocardial necrosis and death at 6 months and 1 year (see e.g., Wong, G. C., et al., Circulation 106: 202 (2002)). Therefore, the development of devices or pharmacologic strategies that preserve tissue perfusion by attenuating the no-reflow phenomenon has important clinical implications.

PCI results in myocardial cell necrosis in 22-44% of patients after an otherwise uncomplicated procedure irrespective if the procedure is elective for stable angina or emergent for ACS (see e.g., Ali, O. A., et al., Am. Heart J. 152: 207 (2006); Johansen, O., et al., Eur. Heart J. 19: 112 (1998)). Elevations of cardiac enzymes (for example creatine kinase-myocardial band (CK-MB) and Troponin I) significantly increase the risk of early and late mortality and myocardial infarction (see e.g., Cavallini, C., et al., Eur. Heart J. 26:1494

(2005); Antman, E. M., et al., N. Engl. J. Med. 335: 1342 (1996)). Furthermore increasing levels of cardiac enzymes are associated with parallel increases in mortality (see e.g., Antman, E. M., et al., N. Engl. J. Med. 335: 1342 (1996); Brener, S. J., et al., Eur. Heart J. 23: 869 (2002)). MRI studies have confirmed that mild increases in CK-MB after PCI are due to microinfarction secondary to embolic microvascular obstruction (see e.g., Ricciardi. M. J., et al., Circulation 103: 2780 (2001)). PCI with stent deployment amplifies myonecrosis probably secondary to increased vascular trauma and release of vasoconstrictor mediators such as serotonin (see e.g., Lesoco, D., et al., Am J. Cardiol. 84:1317 (1999)). While preloading with a potent thienopyridine platelet inhibitor (600 mg of clopidogrel) reduced cell necrosis in a large study, 14% of patients continued to manifest evidence of microembolization (see e.g., Patti, G., et al., Circulation 111: 2099 (2005)). Therefore the common occurrence of embolization during routine interventional procedures provides further impetus to develop improved modalities to reduce this important complication.

In an attempt to reduce the incidence of macro- and microembolization after PCI, numerous pharmacological therapies and embolic and thrombectomy devices have been utilized in patients with STEMI. A potent glycoprotein IIa/IIIb inhibitor failed to reduce infarct size and improve tissue perfusion after PTA or primary stenting in STEMI patients (see e.g., Antoniucci, D., et al, J. Am. Coll. Cardiol. 42: 1879 (2003); Constantini, C. O., et al., J. Am. Coll. Cardiol. 44: 30 (2004)). In the EMERALD trial, the GuardWire distal balloon occlusive device did not improve tissue perfusion or decrease infarct size in 501 patients with STEMI undergoing PCI within 6 hours of symptoms (see e.g., Stone, G. W., et al., JAMA 293: 1063 (2005)). This occurred in spite of use of anti-platelet agents and removal of embolic debris in the majority of patients. The FilterWire system, which consists of a guide wire that incorporates a non-occluding polyurethane porous membrane filter in the shape of a wind sock, has been evaluated in two studies. In one study (hereinafter referred to as the "PROMISE study") no difference in infarct size or tissue perfusion assessed with flow velocity was observed in the FilterWire group in 200 patients with NSTEMI and STEMI (see e.g Gick M., et al., Circulation 112:1462 (2005)). Similar findings were observed in a second study (hereinafter referred to as the "DEDICATION study") where 676 patients with STEMI underwent PCI with and without distal protection. The filter wire system failed to improve ST segment resolution, regional ventricular function or major adverse cardiac events at 30 days (see Kelbaek, et al., J. Am. Coll. Cardiol. 51: 899 (2008).

A number of thrombectomy devices have also been utilized as an adjunct to PCI in STEMI. These include the X-Sizer system (consists of wire system with a helical shaped cutter and aspiration catheter), several aspiration devices (Diver, Export, Rescue catheter) and the angiojet rheolytic thrombectomy system in which high-velocity saline is directed back into the catheter. Eight trials have been conducted with the majority being small (see e.g., Brodie, B. R., J. Invasive Cardiol. 18: 24C (2006); Baim, D. S., J. Invasive Cardiol. 18: 28C (2006)). The two largest trials did not show improved tissue perfusion and one showed larger infarct size compared to control (see e.g., Kaltoft, A., et al., Circulation 114: 40 (2006); Ali, A., et al., J. Am. Coll. Cardiol. 48: 244 (2006)). These findings demonstrate that the current protective and embolic devices are not optimal in achieving complete thrombectomy or preventing distal embolization. Furthermore, they support the concept that other mechanisms, such as humoral factors and cytotoxic compounds, may also be playing an important role in microvascular damage after STEMI.

Prior to the introduction of PCI and stents, CABG was the most frequently utilized procedure to relieve myocardial ischemia in patients with coronary artery disease. However, 50-60% of SVG's develop severe significant atherosclerosis within ten years of surgery requiring catheter based intervention (see e.g., Bourasa, M. G., et al., Circulation 72: V71 (1985); Lau, G. T., et al., Semin. Vasc. Med. 4: 153 (2004)). The soft and friable nature of the lipid rich plaque in SVGs contributes to the frequent embolization of atherothrombotic material after PCI (see e.g. Popma, J. J., Cathet. Cardiovasc. Intervent. 57: 125 (2002); Webb, J., et al., J. Am. Coll. Cardiol. 34: 461 (1999); Safian, R. D., Prog. Cardiovasc. Dis. 44; 437 (2002)). Platelet clumping with subsequent activation and release of the potent vasoconstrictor serotonin may also reduce flow in the distal vascular bed. PCI of degenerated SVG's is associated with significant (~20%) risk of major adverse clinical events (MACE), predominantly myocardial infarction and no-reflow (see e.g. Piana, R. N., et al., Circulation 89: 2514 (1994); de Feyter, P. J., et al., J. Am. Coll. Cardiol. 21: 1539 (1993)). A 3-fold elevation of CK-MB is associated with a 14% 30 day mortality compared with less than 1% without isoenzyme elevation (see e.g. Hong, et al., Circulation 100: 2400 (1999); Lefkovitz, J., et al., Circulation 92: 734 (1995)). Multi-variable predictors of MACE include the extent of graft disease (graft length disease and plaque volume), number of stents inserted and age of the patient (see e.g., Stone, G. W., et al., Circulation 108: 548 (2003)). The high peri-procedural complication rate has necessitated the use of adjunctive therapies to reduce the high adverse event rates. Administration of the IIb/IIIa platelet inhibitor (abciximab) and the thrombectomy catheter (X-sizer) failed to reduce MACE at thirty days (see e.g. Ellis, S. G., et al., J. Am. Coll. Cardiol. 32: 1619 (1998)). In contrast, the GuardWire, FilterWire and a proximal embolic protection system (Proxis) produced significant and equivalent reductions in peri-procedure complications at 30 days (see e.g., Stone, G. W., et al., Circulation 108: 548 (2003); Baim, D. S. et al., Circulation 105: 1285 (2003); Mauri, L., et al., J. Am. Coll. Cardiol. 50: 1442 (2007)). However, peri-procedural complications still occurred in ~10% of patients with these devices emphasizing the need for complimentary devices and/or new pharmacologic interventions.

PCI (PTA, stents) may also compromise blood flow in the subacute and chronic phase following an uneventful procedure. Abnormal vasomotor responses are invariably present after PTA and life threatening vasospasm has been observed at variable times after stent implantation (see e.g., Fischell, T. A., et al., J. Clin. Invest. 86:575 (1990); Brott, B. C., et al., J. Invasive Cardiol. 18:584 (2006)). Drug eluting stents (DESs) are currently the most frequently deployed stent in the USA and consist of a metal stent, polymer and impregnated drug; either an antineoplastic agent, paclitaxel (Taxus) or antiproliferative agents such as sirolimus (Cypher) and zotarolimus (Endeavor). DESs are associated with a small but potentially lethal increase in sub-acute and chronic thrombosis when compared with bare metal stents (BMSs) (see e.g., Camenzind, E., et al., Circulation 115:1440 (2007)). DESs activate pro-coagulant factors and may diminish the ability to develop collateral vessels with stent thrombosis (see e.g., Salloum, J. et al., J. Intervent. Cardiol. 17:575 (2005); Meier, P., et al., J. Am. Coll. Cardiol. 40:21 (2007)). A recent study demonstrates long term adverse effects of DES on endothelial cell function. Vasodilatory responses to acetylcholine were significantly impaired in segments distal to both paclitaxel and sirolimus stents when compared to BMS or a reference non stented vessel 6 months after implantation (see e.g., Kim, J. W., et al., J. Am. Coll. Cardiol. Intv. 1:65 2008). The hypothesis that chronic endothelial dysfunction may result in recurrent ischemia and late stent thrombosis is supported by two studies. In the BASKET study utilizing Taxus stents, cardiac death and infarction at 6 to 18 months was approximately four times greater in the DES arm compared with BMSs (see e.g., Pfasterer, M., et al., J. Am. Coll. Cardiol. 48:2584 (2006)). Recently, a post hoc analysis of the RRISC Trial revealed a significant increase in mortality with Cypher stents implanted in SVGs after a median follow-up of 32 months (see e.g., Vermeersch, P. et al., J. Am. Coll. Cardiol. 50:261 (2007)). Pathological studies with DESs have invariably shown incomplete endothelialization on strut surfaces extending beyond 40 months after implantation with extensive fibrin deposition (see e.g., Joyner, M., et al., J. Am. Coll. Cardiol. 48:193 (2006)). Chronic inflammatory cells (lymphocytes, macrophages and eosinophils) in the intima and media are also present in late stent thrombosis. Release of numerous vasoconstrictors and platelet aggregatory substances by these cells may also contribute to late stent thrombosis. The histological changes observed have been attributed to either direct toxicity and/or delayed hypersensitivity reaction to the drug or polymer, or excessive barotraumas (see e.g., Togni, M., et al., J. Invasive Cardiol. 18:593 (2006)). Local delivery of high concentrations of the physiological nucleotide adenosine that rapidly accelerates endothelial healing, prevents thrombus formation, reduces inflammatory cell infiltration and promotes new vessel formation would have important clinical implications.

While newer DESs are currently undergoing safety and efficacy trials, it appears likely that they will be associated with comparable side effects to the two currently approved stents due to their similar structure and mode of action. In Europe, BMSs are being increasingly utilized in large vessels (>3 mm) and in non-diabetic patients. While late stent thrombosis is rare, restenosis remains a significant problem with BMSs with an incidence of 17 to 25% in non-diabetics and 23 to 33% in diabetics with vessels of 3 mm. Since adenosine is a potent inhibitor of vascular smooth muscle proliferation and extracellular matrix production, it may prove useful in preventing restenosis following BMS implantation.

Carotid revascularization utilizing surgically performed carotid endarterectomy (CEA) has been shown to reduce stroke rate compared with medical therapy in patients with significant (greater than 50%) atherosclerotic narrowing of the carotid bifurcation and internal carotid artery (see e.g. Halliday, A., et al., Lancet 363: 1491 (2004); North American Symptomatic Trial Collaborators, N. Engl. J. Med. 325: 445 (1991)). The rapid development of catheter based technology has resulted in the evaluation of carotid artery stenting (CAS) as an alternative therapy to CEA (see e.g., Roubin, G. S., et al., Circulation 113: 2021 (2006)). CAS has now been approved by the Center for Medicare and Medicaid for patients who are at high risk for CEA (see e.g., Yadav, J. S., J. Am. Coll. Cardiol. 47: 2397 (2006)). Peri-procedural neurological and cardiovascular events remain the main complication of both procedures. Clinically silent micro-embolization occurred in 92% of patients undergoing CEA utilizing transcranial Doppler studies (see e.g., Grant, M., et al., Br. J. Surg. 8: 1435 (1994)). Similarly, 29% of patients manifested silent embolic events after CAS utilizing MRI (see e.g., Jaeger, H., Am. J. Neuroradiol. 23: 200 (2002)). The introduction of EPDs, which are now considered the standard of care, have reduced (by 50%), but not eliminated, embolization of atheromatous debris into the cerebral circulation after stenting (see e.g., Wholey, M. H., and Al-Mubarek, N., Catheter Cardiovasc. Intervent. 60: 259 (2003)). CAS with EPD in high risk patients, in whom a non-surgical approach is preferred due to lower morbidity and mortality, results in approximately 6-12% incidence of major adverse cardiac and cerebral vascular events (see e.g., Safian, R. D., et al., J. Am. Coll. Cardiol. 47: 2384 (2006); Yadav, J. S., et al., N. Eng. J. Med. 351: 1493 (2004)). Low risk patients undergoing CAS with EPD manifest an event rate of 2-3% (see e.g., Zahn, R., et al., Eur. Heart J. 25: 1550 (2004); Kastrur, A., et al., Stroke 34: 813 (2003)). Complications remain high in the elderly (>80 years) with approximately 17.1% incidence of death or stroke at 30 days (see e.g., Hobson, R. W., et al., J. Vasc. Surg. 40: 1106 (2004)).

The reasons why EPDs are not fully protective are multifactorial. Atheromatous material may be dislodged from the aortic arch or common carotid artery during manipulation of the guide catheter and wire prior to the insertion of the EPD. The EPDs are bulky and may induce further embolization during deployment in calcified and tortuous vessels. While EPD devices are universally beneficially, the duration of the deployment significantly increase the risks of complications. For example, deployment of the Filter protection device greater than 20 minutes has been shown to double the risk of death and stroke compared with deployment times of less than 20 minutes (see e.g., Yadav, J. S., Circulation 47: 2397 (2006)). The device may also produce vascular damage (endothelial dysfunction and dissection) and result in incomplete capture or retrieval of debris. Finally, humoral factors released during deployment of the EPD and stent may result in vasospasm or hyperperfusion syndrome, the latter being responsible for 1.3% of intracranial hemorrhage in high risk patients (see e.g., Abou-Chebl, et al., J. Am. Coll. Cardiol. 43: 1596 (2004)).

Renal artery stenosis is a progressive disease associated with high morbidity and mortality and therefore mandates the use of aggressive treatment to improve prognosis (see e.g., Hansen, K. J., et al., J. Vasc. Surg. 36: 443 (2002); Pasternak, K. J. et al., Circulation 109: 2605 (2004)). Renal artery stenting (RAS) has emerged as the treatment of choice due to its excellent success rate and good long term patency (see e.g., Isles, C. G, et al., Q. J. M. 92: 159 (1999)). A major concern is the 20-30% deterioration of renal function after RAS, the highest incidence in patients with underlying renal dysfunction and in those undergoing stent placement compared to PTA (see e.g., Dorros, G., et al., Am. J. Cardiol. 75: 1051 (1995); Leertouwer, T. C., et al., Radiology 216: 7885 (2000); Guerrero, B., et al., Am. J. Cardiol. 90: 63H (2002)). While the etiology of renal dysfunction after RAS is multifactorial, athero-embolism plays an important role over the 3-8 weeks after the procedure (see e.g., Scolari, F., et al., Am. J. Kidney Dis. 36: 1089 (2000)). Most renal lesions involve extensive atheromatous disease of the aorta which amplifies the chance of plaque detachment during the interventional procedure through cholesterol crystal embolization. The high occurrence of embolization has recently been confirmed with EPD where atheromatous debris is captured in greater than 80% of cases (see e.g., Henry, M., et al., J. Endovasc. Ther. 8: 227 (2001)). Atheroembolism has also been shown to adversely affect survival. Since EPDs have only been used in a few small non-randomized series, their long-term effects on renal function and mortality are unknown (see e.g., Henry, et al., Catheter Cardiovasc. Interv. 60: 299 (2003); Hayspiel, K. D., et al., J. Vasc. Interv. Radiol. 16: 125 (2005)). Numerous limitations are present in deployment of EPDs in renal vessels compared with coronary and carotid vessels. Deployment may be difficult due to the sharp angulation of the renal artery from the aorta and its early bifurcation. Furthermore, incomplete capture of embolic debris is more likely in the renal vasculature due to the high incidence of cholesterol crystal embolizations which due to their small size are not captured by EPDs and by the frequent occurrence of branching of the renal vessels.

Vascular occlusive disease of the femoropopliteal system is a frequent cause of claudication and critical limb ischemia in patients with peripheral arterial disease. Percutaneous interventional procedures are frequently utilized in patients with peripheral vascular disease and are complicated by significant peripheral emboli in up to 5% of cases which may lead to serious complications such as amputation or emergency bypass surgery (see e.g., Lin, P. H., et al., J. Surg. Res. 103: 153 (2002); Uher, P., et al., J. Endovasc. Ther. 9: 67 (2002)). Embolization occurs more frequently in high risk patients (up to 37%) such as after thrombolytic therapy or with mechanical thrombectomy (see e.g., Rickard, M. J., et al., Cardiovasc. Surg. 5: 634 (1997)). Macroscopic debris was retrieved in all cases in a small series undergoing an interventional procedure for femoral occlusion (see e.g., Siablis, D., et al., Eur. J. Radiol. 55: 243 (2005)). This has resulted in the use of EPDs in a few high risk patients undergoing interventions (see e.g., Wholey, M. H., et al., Catheter Cardiovasc. Inter. 64:227 (2005)). The current role of EPDs in peripheral vascular disease remains to be determined. The limitations of these devices are likely to be comparable to interventions in other vascular beds. Additional disadvantages include loss of lesion location and potentiation of thrombus formation with occlusive balloon devices, incomplete sealing and excessive movement with subsequent vasospasm with filter devices and technical inability to place the device due to the small size of the femoropopliteal system (see e.g., Wholey, M., et al., Endovascular Today, June: 67 (2007)). These limitations support the need for further technical advances in this field.

Adenosine is an endogenous nucleoside that functions as a local hormone and is found in numerous tissues and organs throughout the body. Adenosine, through activation of four well characterized receptors ($A_1$, $A_{2A}$, $A_{2B}$ and $A_3$), ameliorates many of the adverse processes activated during vascular interventional procedures and thereby exerts multiple protective effects. The protective effects of adenosine include: (a) preservation of microcirculatory flow by reversing the affects of numerous potent vasoconstrictors present in the atherosclerotic ischemic vessel through adenosine's powerful vasodilatory properties; (b) inhibition by adenosine of vascular thrombosis and embolization via adenosine's anti-platelet effects and its ability to restore the profibrinolytic activity of endothelial cells; (c) reduction by adenosine of the cytotoxic effects of free radicals and activated neutrophils; (d) restoration by adenosine of cellular calcium homoestasis; (e) promotion by adenosine of vessel repair (vasculogenesis) and acceleration of the development of new blood vessels (angiogenesis); (f) preservation of vascular patency of interventional site (PTC and/or stent) by limiting intimal hyperplasia via inhibition of vascular smooth muscle cell proliferation and extracellular matrix production (see e.g., Forman, M. B., et al., Cardiovasc Res. 27: 9 (1993); Forman, M. B., et al Cardiovasc. Drug Reviews 24: 116 (2006)). Thus adenosine would be expected to attenuate the no-reflow phenomenon via multiple mechanisms with reversal of vasoconstriction and anti-platelet activity being paramount. The latter is supported by the experimental observation that adenosine functions as an antithrombotic in the ischemic myocardium. Following low flow ischemia, endogenous adenosine inhibits the formation of thromboemboli formed by platelets and platelet-neutrophil aggregates via inhibition of P-selectin receptors on these cells (see e.g., Minamino, T., et al., J. Clin. Invest., 101: 1643 (1998)).

Two small studies have evaluated the effect of intracoronary adenosine on myocardial cell necrosis following non-urgent PCI in stable and unstable angina. Both an intracoronary infusion or bolus administered via the guide catheter prior to the procedure significantly attenuated the rise in creatine kinase-myocardial band (CK-MB) and Troponin 124 hours after PCI (see e.g., Lee. C.-H., et al., Eur. Heart J. 28:19 (2007); Desmet, W. J., et al., Heart 88: 293 (2002)). The extremely short half plasma life (~1-2 secs) of adenosine coupled with dilutional effects of ostial administration, likely diminished its vascular protective effects when the PCI was performed. Medicating the distal vascular bed before and throughout the procedure with concentrated amounts of the drug would optimize its vascular and cardioprotective effects.

Large doses of intravenous adenosine have been shown to have cardioprotective affects with reperfusion therapies in STEMI (see e.g., Maffey, K. W., et al., J. Am. Coll. Cardiol. 34: 1711 (1999); Ross, A. M., et al., J. Am. Coll. Cardiol. 45: 1775 (2005); Kloner, R. A., et al., Eur. Heart J. 27: 2400 (2006)). However, due to the rapid clearance of the drug, large doses are required to obtain an adequate blood level at the target organ, and results in significant side effects. Therefore, there is a need in the art to provide methods and compositions using adenosine-based technology for attenuating the no-reflow phenomenon and reducing or preventing vascular and organ damage during vascular interventions on various organ systems.

SUMMARY OF THE INVENTION

Disclosed herein are guide wires that attenuate the no-reflow phenomenon by releasing one or more medications into the downstream microvascular bed during a vascular interventional procedure. The medications that can be released from the guide wire include, but are not limited to, adenosine, adenosine analogues, an agonist of one or more of the adenosine receptors, a substance that increases endogenous levels of adenosine by inhibiting adenosine metabolism, a substance that increases endogenous levels of adenosine by inhibiting adenosine transport or any combination of the above.

Also disclosed are other devices that can be impregnated or coated with the above listed medications to improve vascular outcomes. For example, disclosed are catheters, balloons, stents (bare metal or drug-eluting), stent grafts, vascular grafts and patches and intraluminal paving systems that can be impregnated or coated with the above listed medications to improve vascular outcomes.

Also disclosed are various vascular interventional procedures in which the disclosed guide wires can be used. These include, but are not limited to, a vascular interventional procedure that involves the native coronary arteries, involves a saphenous vein bypass graft, involves arteries supplying blood to the brain, involves arteries supplying blood to the kidneys, involves arteries supplying blood to the limbs, involves percutaneous balloon angioplasty, involves stent implantation (both bare metal and drug-eluting stents), involves laser angioplasty devices, involves atherectomy devices, involves rotoblader devices, involves a balloon occlusion system, involves a clot protection system, involves a balloon-drug delivery system or involves a clot removing device.

Also disclosed are guide wires that attenuate the no-reflow phenomenon by releasing one or more medications into the downstream microvascular bed during a vascular interventional procedure wherein the guide wire is coated with a medication-releasing preparation in which the medication(s) is (are) incorporated. The medications can be released from any of the disclosed devices when the guide wire or medication(s) comes into contact with body fluids. Alternatively, the medication(s) can be released thorough other physical means.

Also disclosed are guide wires that attenuate the no-reflow phenomenon by releasing one or more medications into the downstream microvascular bed during a vascular interventional procedure, wherein the guide wire is coated with a polymer to which the medication is covalently linked and released when in contact with body fluids.

Also disclosed are guide wires that attenuate the no-reflow phenomenon by releasing adenosine (or adenosine analogues) into the downstream microvascular bed during a vascular interventional procedure, wherein the guide wire is coated with a polymer of adenosine (or adenosine analogues), lysine methyl ester and glycerol of the general chemical structure shown in FIG. 6.

Also disclosed are guide wires that attenuate the no-reflow phenomenon by releasing adenosine (or adenosine analogues) into the downstream microvascular bed during a vascular interventional procedure, wherein the guide wire is coated with a polymer of adenosine (or adenosine analogues), lysine methyl ester and cysteine ethyl ester of the general chemical structure shown in FIG. 16.

Also disclosed are guide wires that attenuate the no-reflow phenomenon by releasing adenosine (or adenosine analogues) into the downstream microvascular bed during a vascular interventional procedure, wherein the guide wire is coated with a monomer containing two or more molecules of adenosine (or adenosine analogues), for example the monomers shown in FIGS. 4, 11 and 21.

Also disclosed are guide wires that attenuate the no-reflow phenomenon by releasing adenosine (or adenosine analogues) into the downstream microvascular bed during a vascular interventional procedure, wherein the guide wire is coated with a monomer containing two or more molecules of adenosine (or adenosine analogues) or with a polymer containing adenosine (or adenosine analogues) and in which additional non-covalently linked ("free") adenosine molecules or molecules of adenosine analogues are incorporated.

Also disclosed are guide wires that attenuate the no-reflow phenomenon by releasing adenosine (or adenosine analogues) into the downstream microvascular bed during a vascular interventional procedure, wherein the guide wire is coated with any combination of any of the following: 1) monomers containing two or more molecules of adenosine (or adenosine analogues); 2) polymers containing adenosine (or adenosine analogues); 3) non-covalently linked ("free") adenosine molecules or free molecules of adenosine analogues; 4) medications either free or in monomers or polymers that limit adenosine metabolism or uptake.

Also disclosed is a polymer that releases adenosine (or adenosine analogues) upon contact with body fluids. For example, disclosed is a polymer of adenosine (adenosine analogues), lysine methyl ester and glycerol that releases adenosine (or adenosine analogues) upon contact with body fluids in which the chemical structure can be that shown in FIG. 6.

Also disclosed is a polymer of adenosine (or adenosine analogues), lysine methyl ester and cysteine ethyl ester that releases adenosine (or adenosine analogues) upon contact with body fluids in which the chemical structure is shown in FIG. 16.

Also disclosed are monomers of adenosine (or adenosine analogues) and lysine methyl ester that releases adenosine (or adenosine analogues) upon contact with body fluids in which the chemical structures are shown in FIGS. 4 and 21

Also disclosed is a monomer of adenosine (or adenosine analogues) and lysine methyl ester that releases adenosine (or adenosine analogues) upon contact with body fluids in which the chemical structure is shown in FIG. 11.

BRIEF DESCRIPTION OF THE DRAWINGS

FIG. 15 shows synthesis of polymer of adenosine, lysine methyl ester and cysteine ethyl ester from Adenosine-LDI-Cysteine Monomer.

FIG. 20 shows morphology of coating of polymer of adenosine, lysine methyl ester and cysteine ethyl ester on cardiac guide wire surface. The surface of guide wire was coated by electro-polymerization process using 1 mA for 2 min. Image A showed a smooth film was coated on the guide wire surface. Some nodules were observed by scanning electron micrograph of the same sample at higher magnification (B and C).

DETAILED DESCRIPTION

Figure 1:
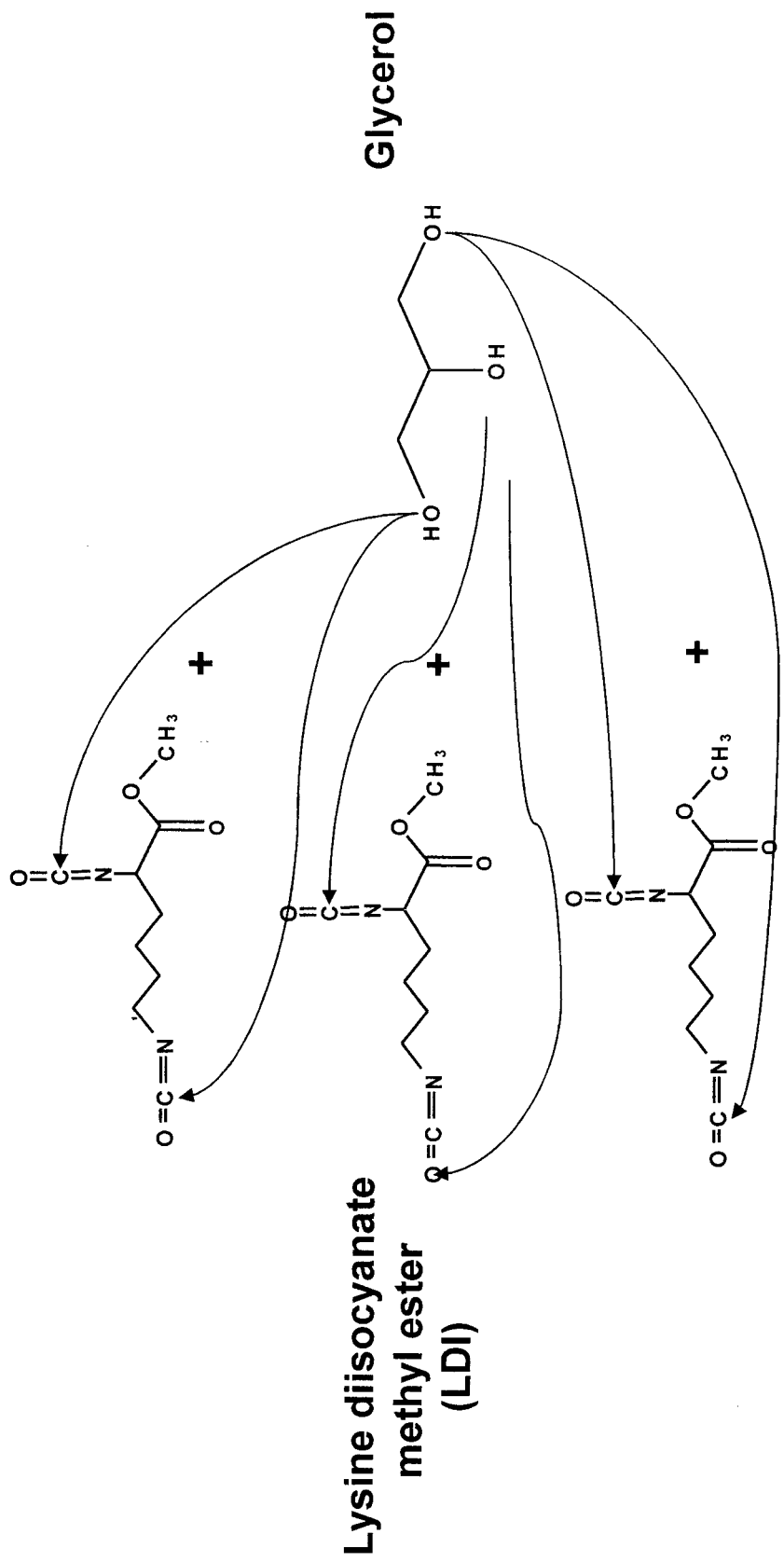
FIG. 1 shows the synthesis of LDI-Glycerol Monomer. Shown in FIG. 1 is nucleophilic oxygen in all three hydroxy moieties of glycerol attacking the electrophilic carbons in one or the other isocyanate groups of LDI to form LDI-glycerol. Three moles of LDI per 1 mole of glycerol ensures monomer of glycerol substituted at all three hydroxy groups. Linkage with LDI can be in one of two orientations, but unimportant with regard to activity. The reaction was monitored by FT-IR.

In this specification and in the claims that follow, reference will be made to a number of terms, which shall be defined to have the following meanings:

By "pharmaceutically acceptable" is meant a material that is not biologically or otherwise undesirable, i.e., the material can be administered to an individual along with the relevant active compound without causing clinically unacceptable biological effects or interacting in a deleterious manner with any of the other components of the pharmaceutical composition in which it is contained.

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

As used throughout, by a "subject" is meant an individual. Thus, the "subject" can include domesticated animals, such as cats, dogs, etc., livestock (e.g., cattle, horses, pigs, sheep, goats, etc.), laboratory animals (e.g., mouse, rabbit, rat, guinea pig, etc.) and birds. In one aspect, the subject is a mammal such as a primate or a human.

The term "no reflow" as described herein refers to the progressive decrease in blood flow during the peri-reperfusion period following a vascular interventional procedure.

The term "guide wire" as described herein refers to a device that crosses the target vascular lesion during a vascular interventional procedure.

The term "adenosine analogue" as described herein refers to any chemical derivative of adenosine. Examples are listed in Table 1 of Chapter 6 (pages 104 through 107) by K. A. Jacobson and A. M. Van Rhee in Purinergic Approaches in Experimental Therapeutics (edited by K. A. Jacobson and M. F. Jarvis, Wiley-Liss, New York, 1997) and in Chapter 6 (pages 130-140) by K. A. Jacobson and L. J. S. Knutsen in Purinergic and Pyrimidinergic Signalling I (editors M. P. Abbracchio and M. Williams, Springer, Berlin, 2001), which are hereby incorporated in their entirety for their teaching of adenosine analogues.

The term "free molecules of adenosine" or "free molecules adenosine analogues" as described herein refers to molecules that are not covalently linked to a monomer or polymer, but are entrapped in the composition as a mixture.

The term "receptor agonist" as described herein refers to a chemical that binds to receptors either on cell surfaces or within cells and causes receptors to trigger a signal transduction process.

Disclosed herein are medical devices for dilation of blood vessels, comprising a composition comprising at least one medication; and a body having at least a portion coated with the composition, wherein the composition is configured for delivery of the at least one medication therein to the blood vessels when in contact with body fluids. The medical devices disclosed herein can further comprise at least one means for attenuating a no-reflow phenomenon. The body of the medical devices disclosed herein can be a guide wire.

Also disclosed herein are medical devices for dilation of blood vessels, comprising a composition comprising at least one medication; and a body having at least a portion coated with the composition, wherein the composition is configured for delivery of the at least one medication therein to the blood vessels when in contact with body fluids, wherein the at least one medication comprises one or more adenosine receptor agonists, at least one medication comprises one or more adenosine analogues, or a combination thereof.

Also disclosed herein are medical devices for dilation of blood vessels, comprising a composition comprising at least one medication; and a body having at least a portion coated with the composition, wherein the composition is configured for delivery of the at least one medication therein to the blood vessels when in contact with body fluids, wherein the at least one medication comprises means for inhibiting the metabolism or uptake of adenosine.

Also disclosed herein are medical devices for dilation of blood vessels, comprising a composition comprising at least one medication; and a body having at least a portion coated with the composition, wherein the composition is configured for delivery of the at least one medication therein to the blood vessels when in contact with body fluids wherein the composition comprises a polymer, a monomer, or a combination thereof.

The medication of the disclosed medical devices can comprise adenosine or adenosine analogues. The composition of the disclosed medical devices can comprise a polymer of adenosine or adenosine analogues, lysine methyl ester and glycerol, with or without the addition of free adenosine or free adenosine analogues.

Also disclosed herein are medical devices for dilation of blood vessels, comprising a composition comprising at least one medication; and a body having at least a portion coated with the composition, wherein the composition is configured for delivery of the at least one medication therein to the blood vessels when in contact with body fluids, wherein the composition comprises a polymer having units of the formula (I):

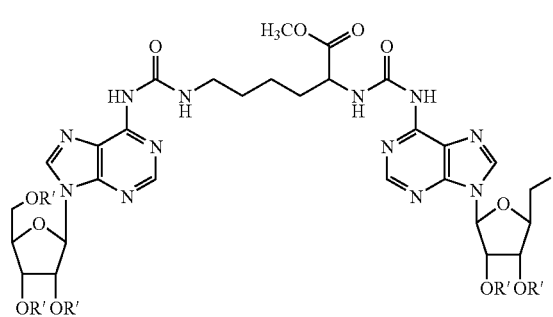

wherein the R's represent the same or different units having the formula (II):

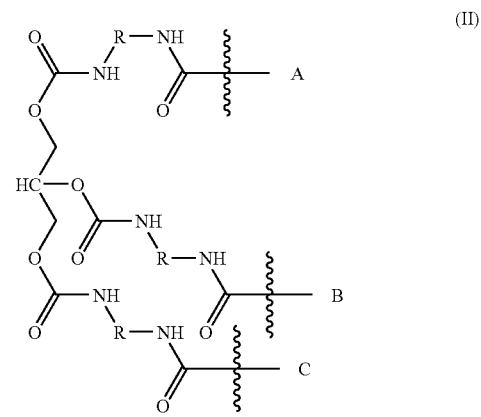

such that the units of formula (II) bond to units of formula (I) through all bonding sites A, B, and C. The A, B and C sites of the R' units can bond to the same ribose ring of a unit of formula (I) or on different ribose rings of a unit of formula (I) to create intramolecular crosslinking or on different ribose rings of different units of formula (I) to create intermolecular crosslinking thus providing a polymer of units of formula (I) bonded together by units of formula (II); and each R is independently a unit having the formula:

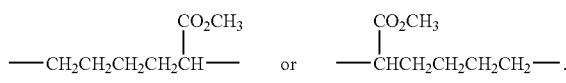

Also disclosed herein are medical devices for dilation of blood vessels, comprising a composition comprising at least one medication; and a body having at least a portion coated with the composition, wherein the composition is configured for delivery of the at least one medication therein to the blood vessels when in contact with body fluids wherein the composition comprises a polymer of adenosine or adenosine analogues, lysine methyl ester and cysteine ethyl ester, with or without the addition of free adenosine or free adenosine analogues.

Also disclosed herein are medical devices for dilation of blood vessels, comprising a composition comprising at least one medication; and a body having at least a portion coated with the composition, wherein the composition is configured for delivery of the at least one medication therein to the blood vessels when in contact with body fluids, wherein the composition comprises a polymer having the formula:

(III)
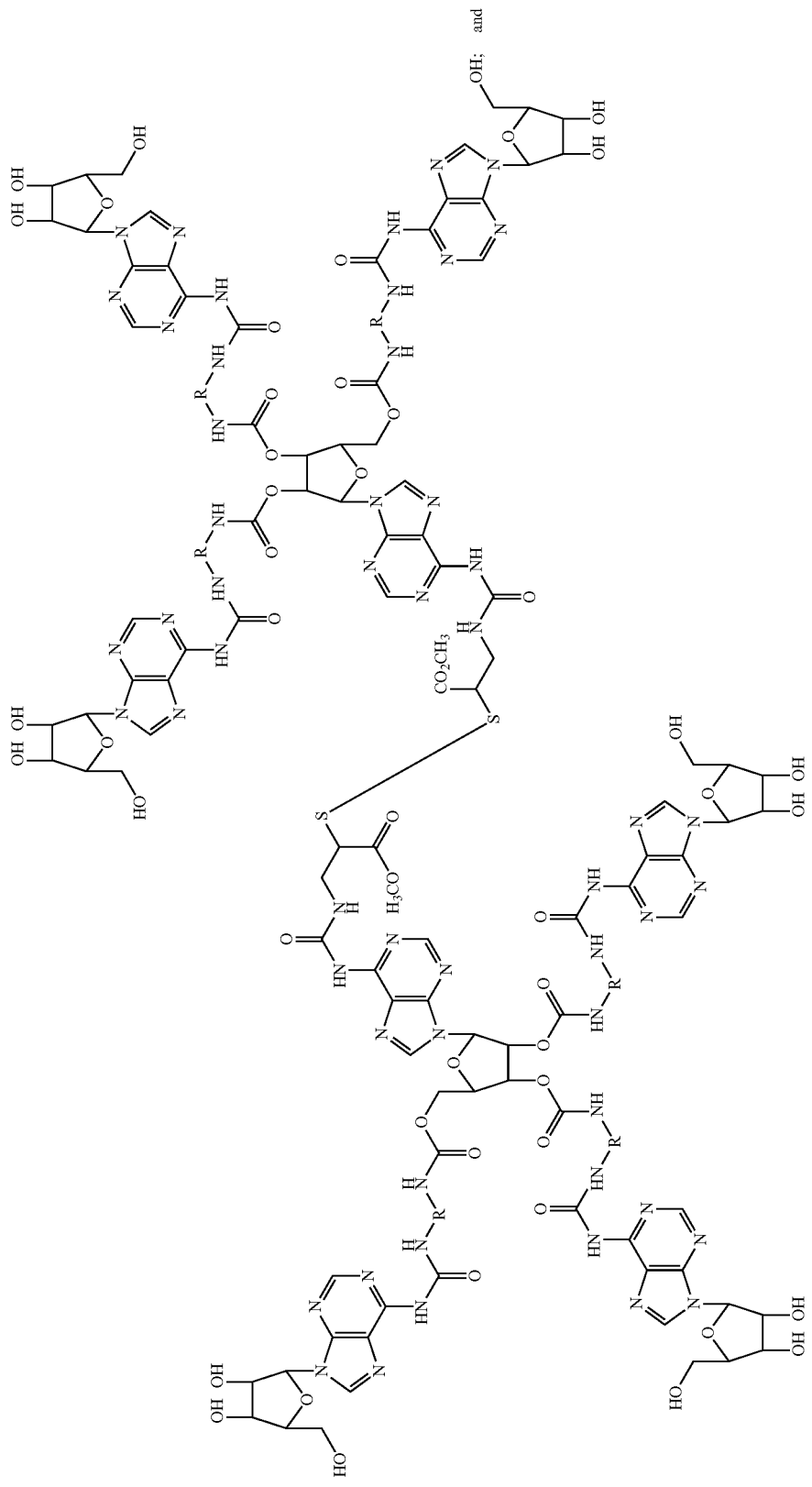

wherein each R is independently a unit having the formula:

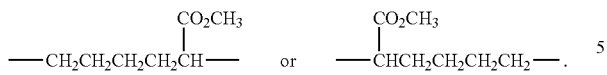

The disclosed medical devices can also comprises a monomer containing two or more adenosine molecules or molecules of adenosine analogues, with or without the addition of free adenosine or free adenosine analogues.

The disclosed medical devices can also comprises a monomer having the formula:

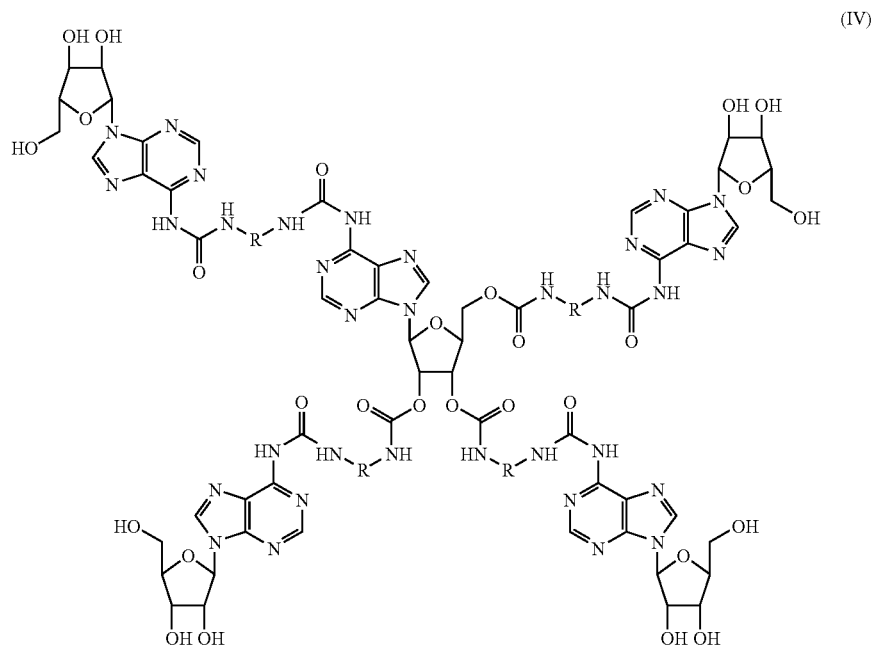

(IV)

wherein each R unit is independently selected from a unit having the formula:

Also disclosed herein are medical devices for dilation of blood vessels, comprising a composition comprising at least one medication; and a body having at least a portion coated with the composition, wherein the composition is configured for delivery of the at least one medication therein to the blood vessels when in contact with body fluids, wherein the composition comprises a monomer having the formula:

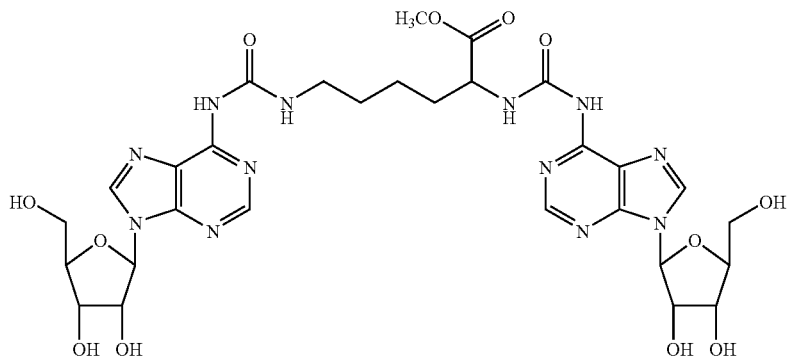 [SMILES: COC(=O)C(CCCCNC(=O)Nc1ncnc2c1ncn2C1OC(CO)C(O)C1O)NC(=O)Nc1ncnc2c1ncn2C1OC(CO)C(O)C1O]

Also disclosed herein are monomers that release adenosine or adenosine analogues upon contact with body fluids. The disclosed monomers can have the formula:

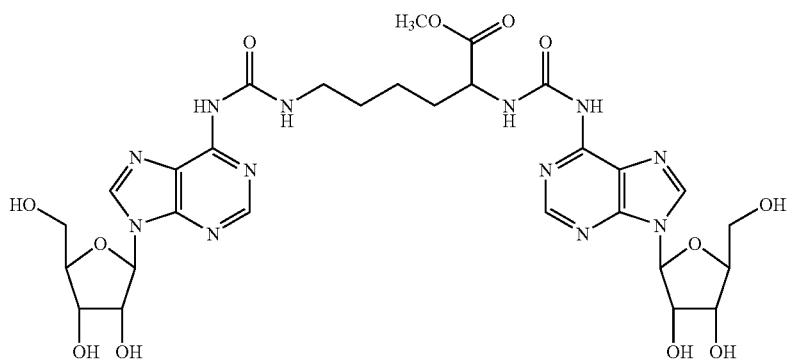 [SMILES: COC(=O)C(CCCCNC(=O)Nc1ncnc2c1ncn2C1OC(CO)C(O)C1O)NC(=O)Nc1ncnc2c1ncn2C1OC(CO)C(O)C1O]

The disclosed monomers can be coated onto a medical device. For example, the disclosed monomers can be coated onto one of the medical devices disclosed elsewhere herein including, but not limited to a vascular stent or guide wire.

The disclosed monomers can have the formula:

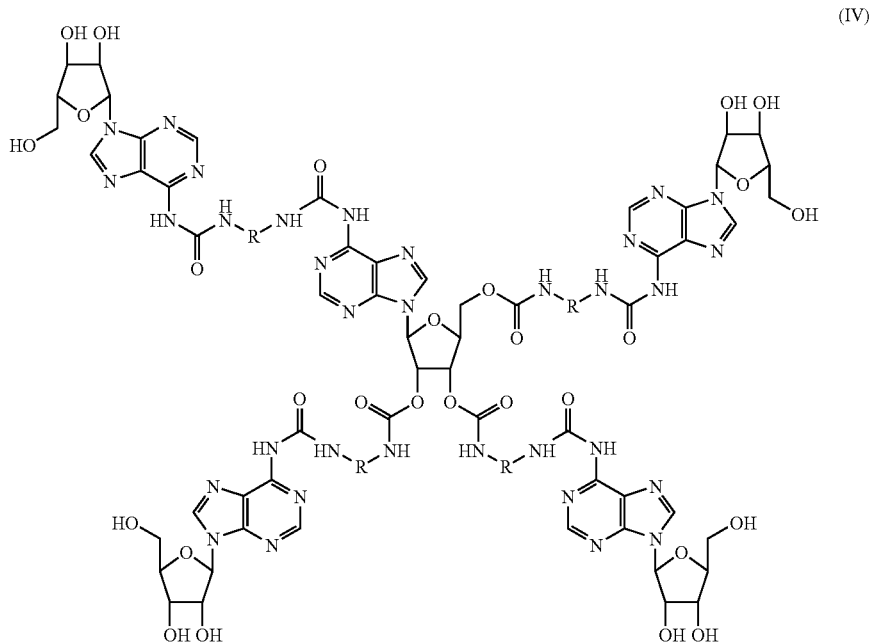

(IV)

wherein each R unit is independently selected from a unit having the formula:

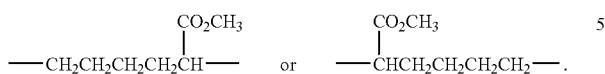

Also disclosed herein are polymers that release adenosine or adenosine analogues upon contact with body fluids. The disclosed polymers can comprise adenosine or adenosine analogues, lysine methyl ester and glycerol. The disclosed polymers can further comprise a device.

The disclosed polymers can also have units of the formula (I):

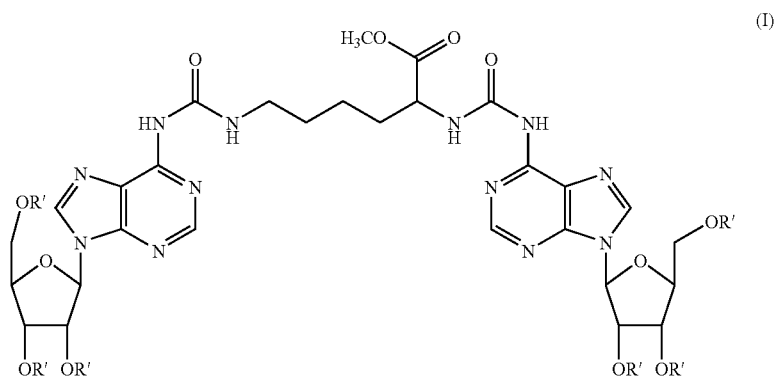

wherein the R's represent the same or different units having the formula (II):

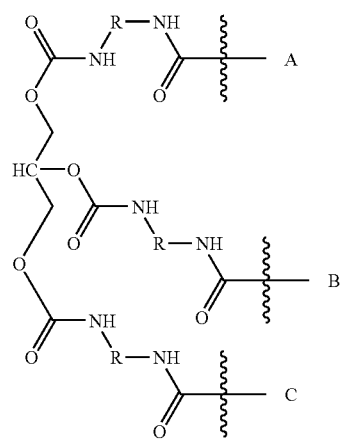

such that the units of formula (II) bond to units of formula (I) through all bonding sites A, B, and C. The A, B and C sites of the R' units can bond to the same ribose ring of a unit of formula (I) or on different ribose rings of a unit of formula (I) to create intramolecular crosslinking or on different ribose rings of different units of formula (I) to create intermolecular crosslinking thus providing a polymer of units of formula (I) bonded together by units of formula (II); and each R is independently a unit having the formula:

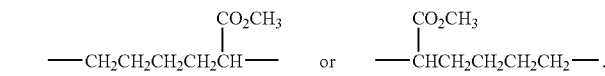

and wherein the polymer coats at least a portion of the device.

The disclosed polymers can be a polymer of adenosine or adenosine analogues, lysine methyl ester and cysteine ethyl ester. The disclosed polymers can be coated onto a medical device. For example, the disclosed polymers can be coated onto one of the medical devices disclosed elsewhere herein including, but not limited to a vascular stent or guide wire.

The disclosed polymers can also have the formula:

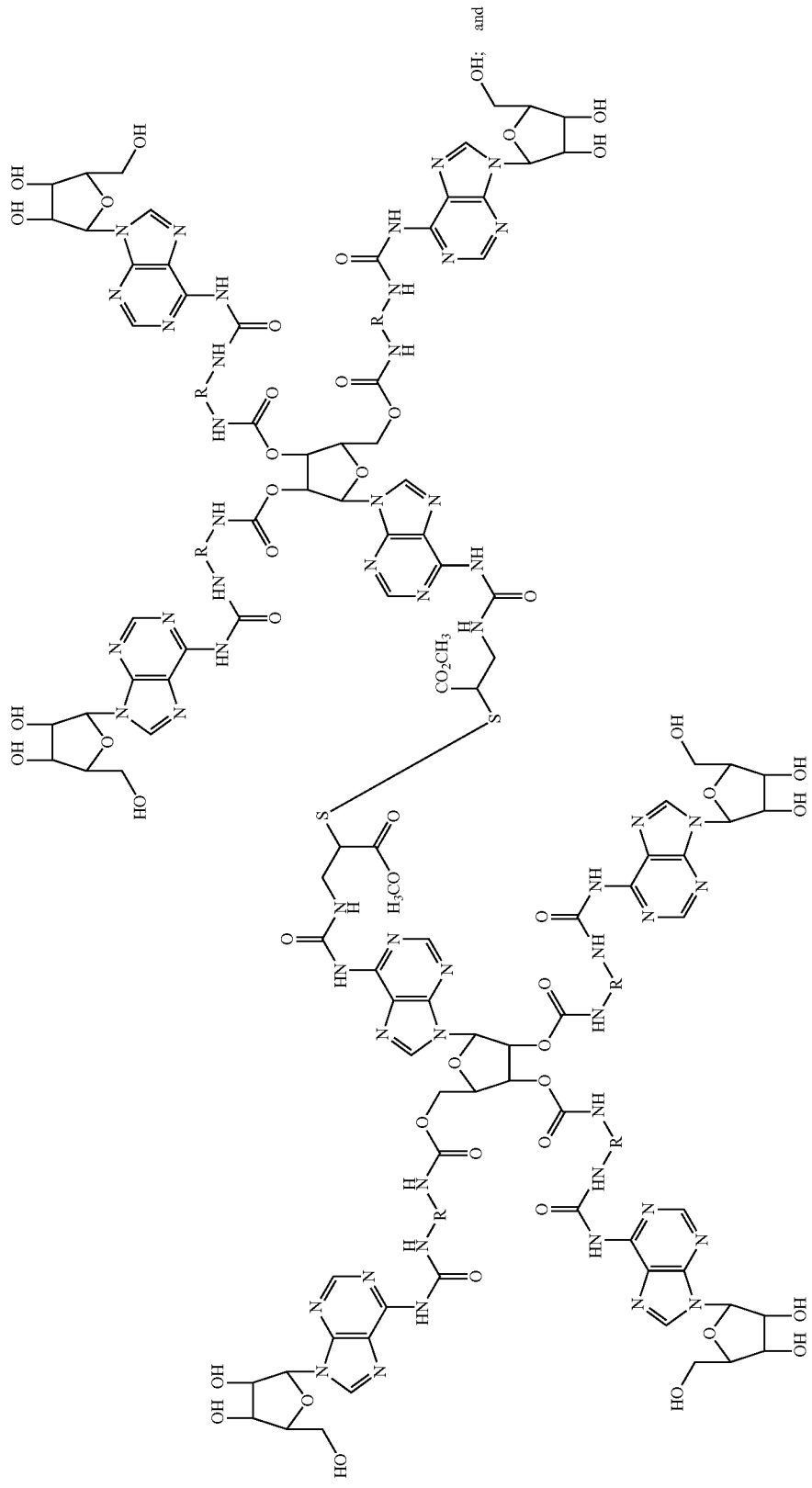

wherein each R is independently a unit having the formula:

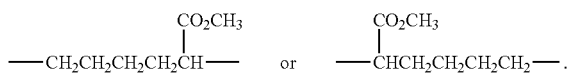

The current standard practice for vascular interventional procedures initially involves relaxing the patient with intravenous sedative and analgesic drugs followed by injection of a local anesthetic agent into the subcutaneous site to be utilized for the arterial puncture (groin or wrist). After making a small subcutaneous incision the artery (usually femoral or radial) is punctured with a hollow vascular needle through which an initial tracking wire is threaded under fluoroscopic (X-ray) guidance. The needle is withdrawn and a vascular sheath is advanced over the initial tracking wire into the artery. The patient is then given an intravenous anticoagulant (heparin or derivative). A guide catheter is placed over the initial tracking wire and is introduced into the sheath and advanced under fluoroscopy close to the target artery. The initial tracking wire is withdrawn, and the guide catheter is connected to a manifold which allows measurement of arterial pressure and injection of fluids and radio-opaque contrast agent into the guide catheter. The guide catheter is manipulated until it engages the orifice of the vessel feeding the diseased artery which is then visualized in multiple views with injection of the radio-opaque contrast agent. A guide wire is inserted into the lumen of the guide catheter and is carefully advanced into the target vessel, across the target lesion and positioned in a stable site in the distal part of the diseased vessel. Thus the guide wire is defined as the first device that actually crosses the target lesion. In cases where the lesion is extremely narrow, pre-dilatation is preferred utilizing a balloon catheter which is advanced over the guide wire until it covers the lesion. The balloon is then inflated with variable pressure (~6-10 atmospheres) until it fully inflates without any narrowing of the artery. This implies that the inflation produced an adequate opening in the vessel by compressing the atheromatous plaque into the media of the vessel wall. Multiple inflations with the same or larger balloons may be required to obtain an adequate opening of the narrowed artery. In patients with ostial, heavily calcified or restenotic lesions, which are due to excessive scar tissue from a prior procedure, use of other devices such as a rotoblader, atherectomy, or cutting balloon may be needed to produce adequate opening of the diseased artery. Following the initial procedure, an appropriately sized stent (both bare metal and drug-eluting and usually pre-mounted on a balloon catheter) is usually placed to optimize the opening of the blockage. After removal of the pre-dilatation balloon or device, the stent catheter is advanced over the guide wire across the lesion in the same way as the balloon catheter and inflated at the recommended pressure. Intravascular ultrasound (IVUS) may be utilized by the physician both before and after the procedure. In the former, IVUS may be helpful in assessing the size of the diseased vessel and the severity, extent and morphology of the atheromatous plaque; in the latter it helps confirm that the stent struts are adequately apposed to the inner lining of the vessel wall. If the stent is not fully deployed, the stent balloon is removed and a high pressure balloon is advanced over the guide wire and inflated across the stent. IVUS may then be repeated to confirm satisfactory stent expansion. The stent or balloon catheter, guide wire and guide catheter are then removed and the patient is returned to his/her room. After several hours have elapsed to allow for anticoagulation therapy given during the procedure to reverse, the sheath is removed and hemostasis achieved with manual or mechanical pressure. Unless an entry site closure device has been used, the patient will remain at bed rest for several hours after sheath removal to allow sufficient time for the puncture site to seal.

The present invention relates to methods and compositions for reducing, preventing or reversing vascular and organ damage and improving outcomes during various vascular interventional procedures. For example, the present invention relates to methods and compositions for reducing, preventing or reversing vascular and organ damage and improving outcomes during vascular interventional procedures on various organs utilizing an anti-no-reflow guide wire designed to attenuate the no-reflow phenomenon by rapidly releasing one or more medications into the downstream microcirculation during all or part of the interventional procedure. The concept of this invention is to coat the guide wire in such a manner as to release one or more medications immediately following contact with blood in the vascular compartment. The medication(s) can be incorporated into the distal end of the guide wire resulting in an immediate, continual and concentrated release of the medicant(s) into the vascular tree distal to the culprit lesion being treated with the mechanical intervention. Thus, the vascular bed can be prophylactically medicated prior to the performance of the mechanical procedure. The high concentration of the medicant(s) in the distal bed prevents or reverses damage to the vascular tree induced by the release of embolic debris and/or humoral mediators following disruption of the atheromatous plaque by the mechanical intervention. Because, by definition, the guide wire is the first device that crosses the vascular lesion, the medication(s) will immediately influence the distal vasculature to improve outcomes. The present invention accomplishes direct, intra-artery administration of medications without the need for further injections of drugs by the physician and without the need for any additional manipulations. The medication can be automatically released from the tip of the guide wire without need for additional considerations by the physician. For example, the medication(s) can be released upon contact with water within the body fluids of a subject. Also, because the medication(s) is (are) released directly into the diseased vascular bed, high concentrations are achievable compared with systemic administration. Furthermore, adverse effects due to systemic administration of the medication(s) can be reduced or completely negated.

Also disclosed herein are methods for preventing, reducing or reversing vascular and organ damage and improving outcomes during vascular interventional procedures on various organ systems with a guide wire designed to release adenosine, or an adenosine analogue, into the blood flow of the downstream vascular bed during the procedure.

Also disclosed are methods for preventing, reducing or reversing vascular and organ damage and improving outcomes during vascular interventional procedures on various organ systems with a guide wire designed to release one or more adenosine receptor ($A_1$, $A_{2A}$, $A_{2B}$ or $A_3$) agonists into the blood flow of the downstream vascular bed during the procedure.

Also disclosed are methods for preventing, reducing or reversing vascular and organ damage and improving outcomes during vascular interventional procedures on various organ systems with a guide wire designed to release one or more medications that increase levels of endogenous adenosine (such as inhibitors of adenosine uptake, inhibitors of adenosine metabolism, inhibitors of adenosine deaminase or inhibitors of adenosine kinase) in the downstream vascular bed or blood feeding the downstream vascular bed during the procedure.

In all embodiments, the anti-no-reflow guide wire can be used in vascular interventional procedures involving arteries and blood vessels supplying blood to the heart, brain, kidneys or peripheral circulation, both native arteries and blood vessels as well as saphenous vein, internal mammary artery and radial artery bypass vessels.

In all embodiments, the anti-no-reflow guide wire can be used in a wide variety of vascular interventional procedures including percutaneous balloon angioplasty, laser angioplasty, stent (bare metal and/or drug-eluting) implantation and atherectomy. In all embodiments, the anti-no-reflow guide wire can be used in conjunction with a number of other devices including rotoblader devices, clot protection devices, clot removal devices and proximal and distal occlusion devices.

The anti-no-reflow guide wire can be designed to release the anti-no-reflow medications beginning immediately upon insertion and continuing throughout the duration of the procedure using a number of approaches including, but not limited to, incorporation of the medication(s) in a polymer from which the medication is released when in contact with body fluids. For example, the medication is covalently linked to the polymer and the medication(s) is (are) released when in contact with body fluids. The example below is provided to illustrate the concept of the disclosed guide wires that can provide immediate and sustained release of adenosine from the wire for the approximate duration of vascular procedure during which pharmacologically active levels of adenosine are achieved when the wire comes in contact with water or blood. However, it should be noted that numerous variations of this concept are possible and the current invention incorporates all variations of this approach including other methods to release the medication(s) and other medications besides adenosine.

EXAMPLES

Example 1

Polyurea coatings technology is a recent development in the polyurethane coatings industry. Polyurethane chemistry has existed for approximately 60 years, while elastomeric urethane coatings have been available since the 1970s. Polyurea elastomer technology was introduced some 10 years later.

Isocyanates are the fundamental starting materials for the synthesis of polyurethanes. The isocyanate group is very reactive towards "active" hydrogens from water, alcohols and amines. Isocyanate terminated pre-polymer polymerizes rapidly in the presence of active hydrogen donor compounds. This capability of rapid polymerization has evoked considerable interest in isocyanates and their use in medical applications. Some researchers have even developed a urethane prepolymer as a tissue adhesive (see e.g., Matsuda et al., ASAIO Trans. 35:381 (1989)). However, commercial isocyanates are toxic due to their degradation products such as aromatic diamines.

Recently, a new generation of polyurethanes composed of lysine diisocyanate and glycerol that degrades into non-toxic components (lysine and glycerol) have been developed (see Zhang et al., Biomaterials 21:1247 (2000)). These peptide-based urethanes possess the versatility of polyurethanes, but lack the toxicity of other urethane degradation products. In Example 1, two pre-polymers were synthesized using lysine diisocyanate, glycerol and adenosine.

Figure 2:
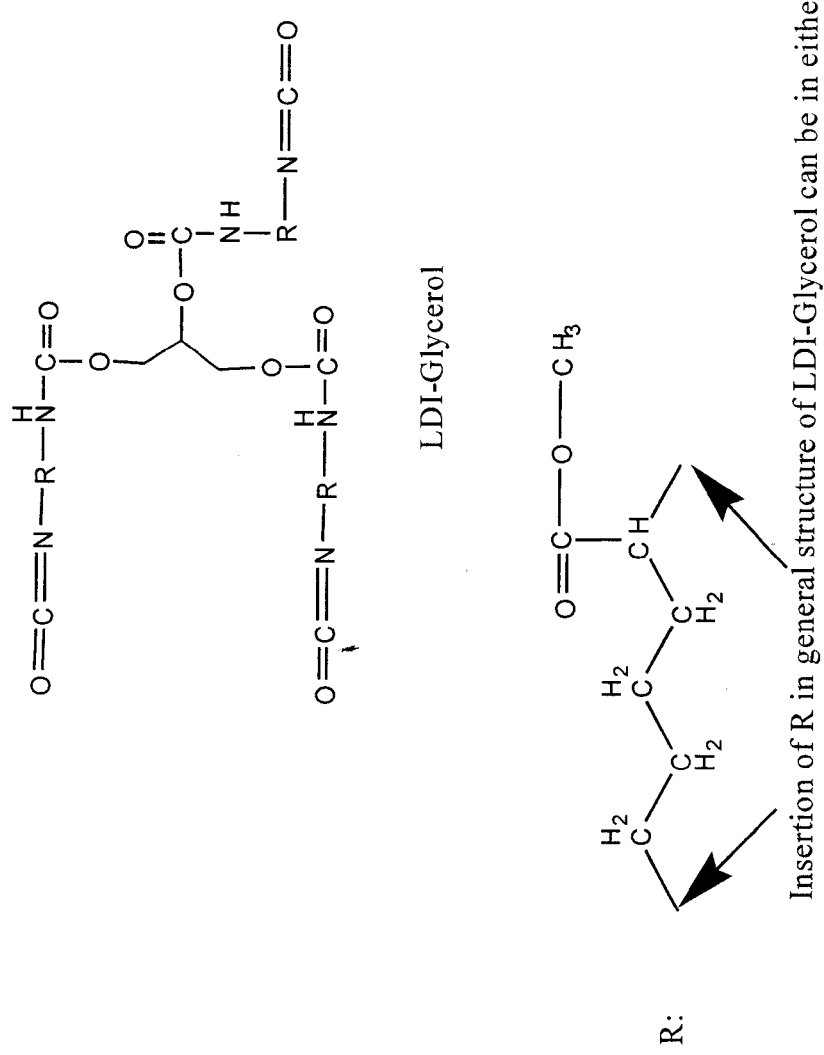
FIG. 2 shows the general structure of LDI-Glycerol Monomer.
Figure 3:
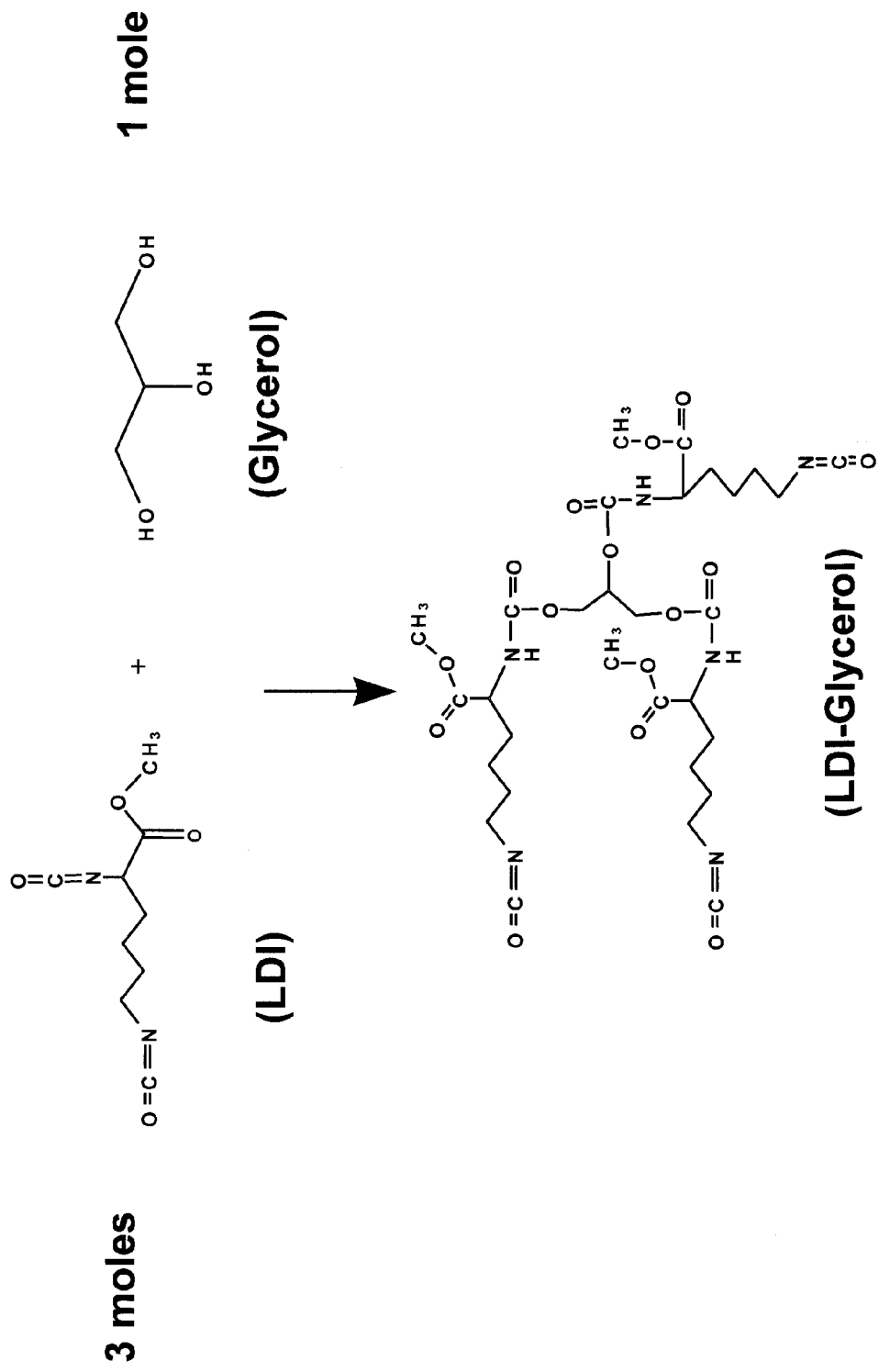
FIG. 3 shows the structure of a specific example of a LDI-Glycerol Monomer.

Lysine diisocyanate methyl ester (LDI) was purchased from Chemical Division, Kyowa Hakko Kogyo Co. Ltd. (Tokyo, Japan). All other reagents were obtained from Aldrich Chemical Co. (Milwaukee, Wis.). The synthetic route to the LDI-Glycerol Monomer using glycerol and LDI is shown in FIG. 1. FIG. 2 illustrates the general structure of the LDI-Glycerol Monomer, and FIG. 3 illustrates an example of a specific LDI-Glycerol Monomer. A typical synthesis was performed by placing 0.50 grams of glycerol and 1 ml of dimethylsulfoxide (DMSO) into a dry round-bottomed flask. The flask was flushed with nitrogen, fitted with rubber septa and sealed. Subsequently, 3 ml of LDI (MW 212, d 1.157, 16.3726 mmoles; —NCO 32.7453 mmoles) were added into the reaction mixture using a syringe. The reaction mixture was stirred in the dark at room temperature for 2 days. The disappearance of the isocyanate groups and the accompanying formation of urethane linkages were monitored by FT-IR. The reaction was stopped when the FT-IR suggested that 50% of isocyanate groups (peak at 2285 $cm^{-1}$) initially present had been consumed. The viscous liquid obtained at this point was called LDI-Glycerol Monomer).

Figure 4:
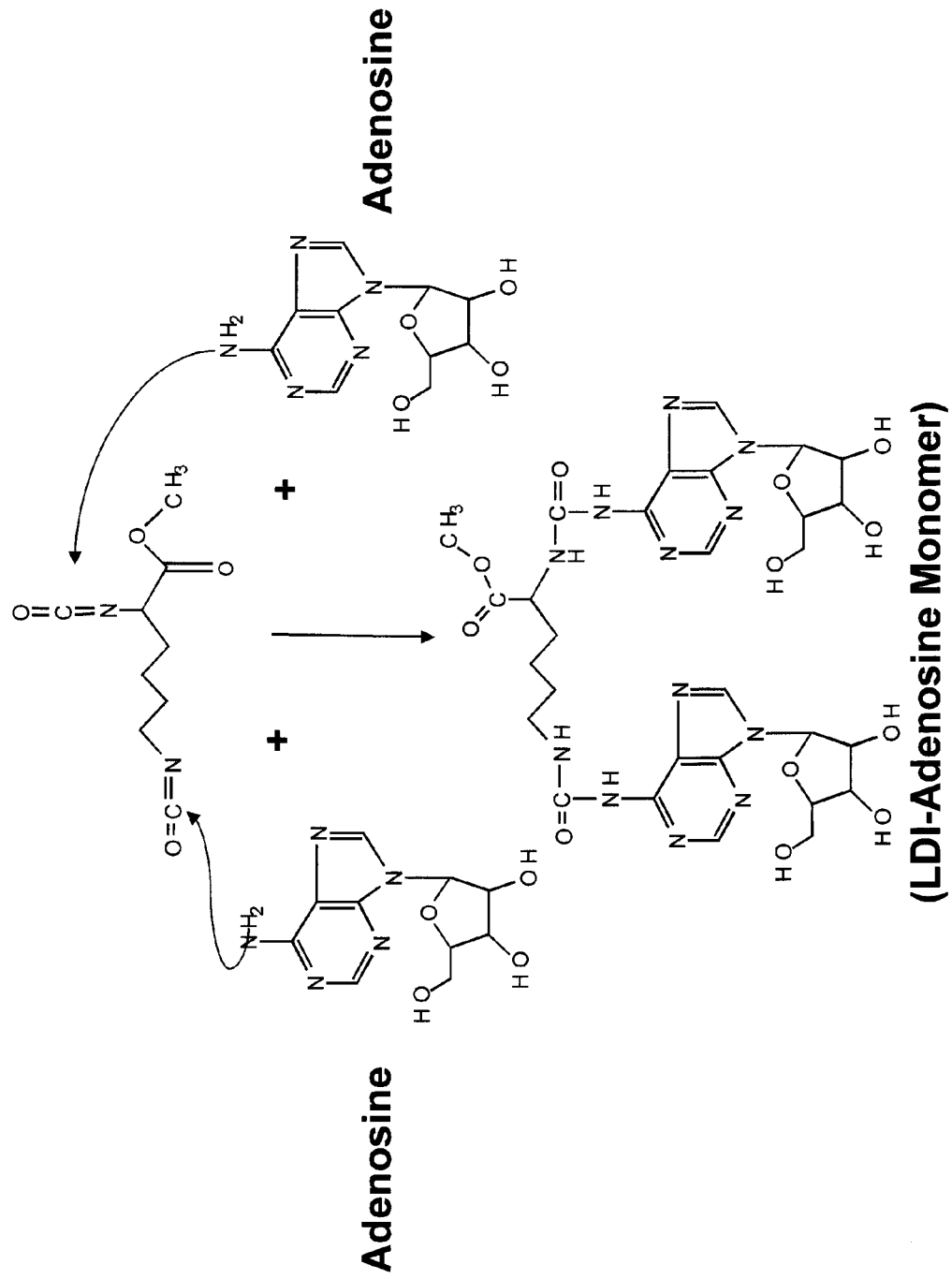
FIG. 4 shows the synthesis of LDI-Adenosine Monomer. Nitrogen in primary amine is much stronger nucleophil than oxygen in hydroxy so linkage is with amino group of adenosine. Two moles of adenosine per 1 mole of LDI ensures linkage of LDI with two molecules of adenosine. The reaction was monitored by FT-IR.

The synthesis of the LDI-Adenosine Monomer is shown in FIG. 4. Typically, 1.33 grams of adenosine (MW 261.04, 5.1 mmoles) and 2 ml of DMSO were placed into a dry round-bottomed flask. The flask was flushed with nitrogen, fitted with a rubber septa and sealed. Subsequently, 0.47 ml of LDI (MW 212, d 1.157, 2.57 mmoles; —NCO 5.1 mmoles) were added to the reaction mixture using a syringe. The reaction mixture was stirred in the dark at room temperature for 2 days. The disappearance of the isocyanate groups and the accompanying formation of urethane linkages were monitored by FT-IR. The reaction was stopped when the FT-IR showed no remaining isocyanate groups. The products were washed three times with distilled deionized water to remove DMSO. The residue was called LDI-Adenosine Monomer.

Figure 5:
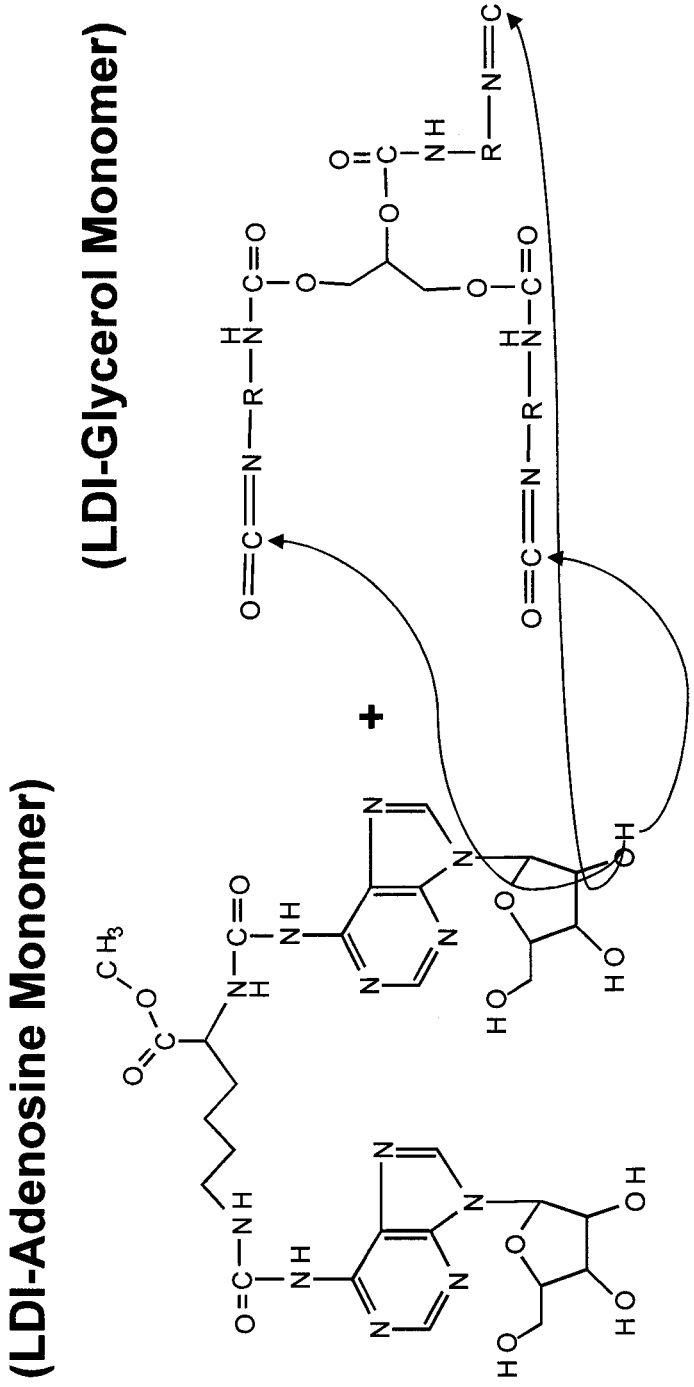
FIG. 5 shows the polymerization between LDI-Adenosine Monomer and LDI-Glycerol Monomer to form a polymer of adenosine, lysine methyl ester and glycerol.
Figure 6:
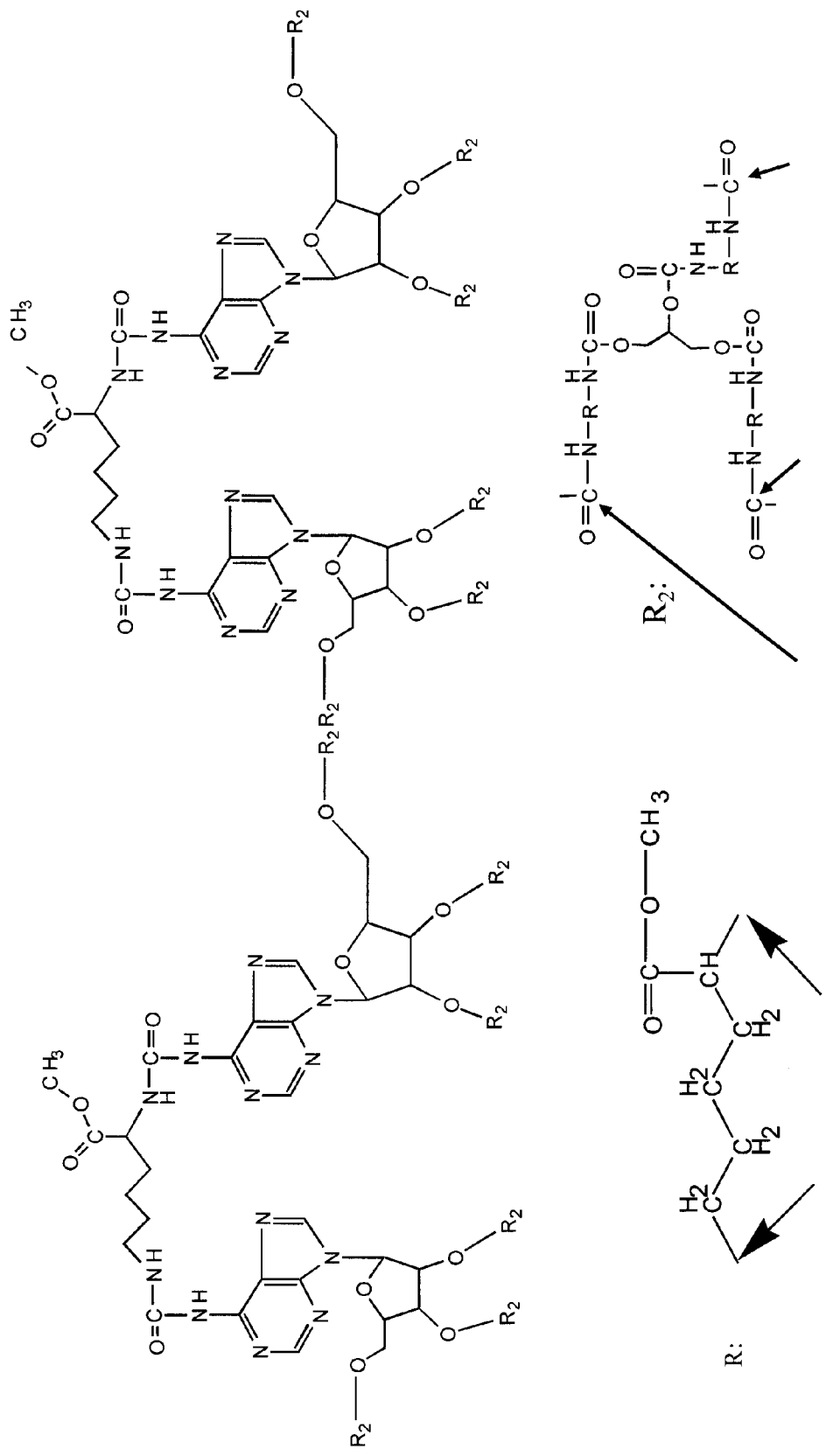
FIG. 6 shows the general structure of the polymer of adenosine, lysine methyl ester and glycerol. The $R_2$ at each indicated site can be different or same. When the $R_2$ at each indicated site is the same, the result can be intramolecular or intermolecular crosslinking resulting in polymer of adenosine, lysine methyl ester, and glycerol. Additionally, adenosine analogues can be substituted for adenosine. Furthermore, the R group in the general structure of $R_2$ can be in either orientation. The ester linkages to $R_2$ in the general structure of the polymer can also be at any of the three ester linkage sites in $R_2$.
Figure 7:
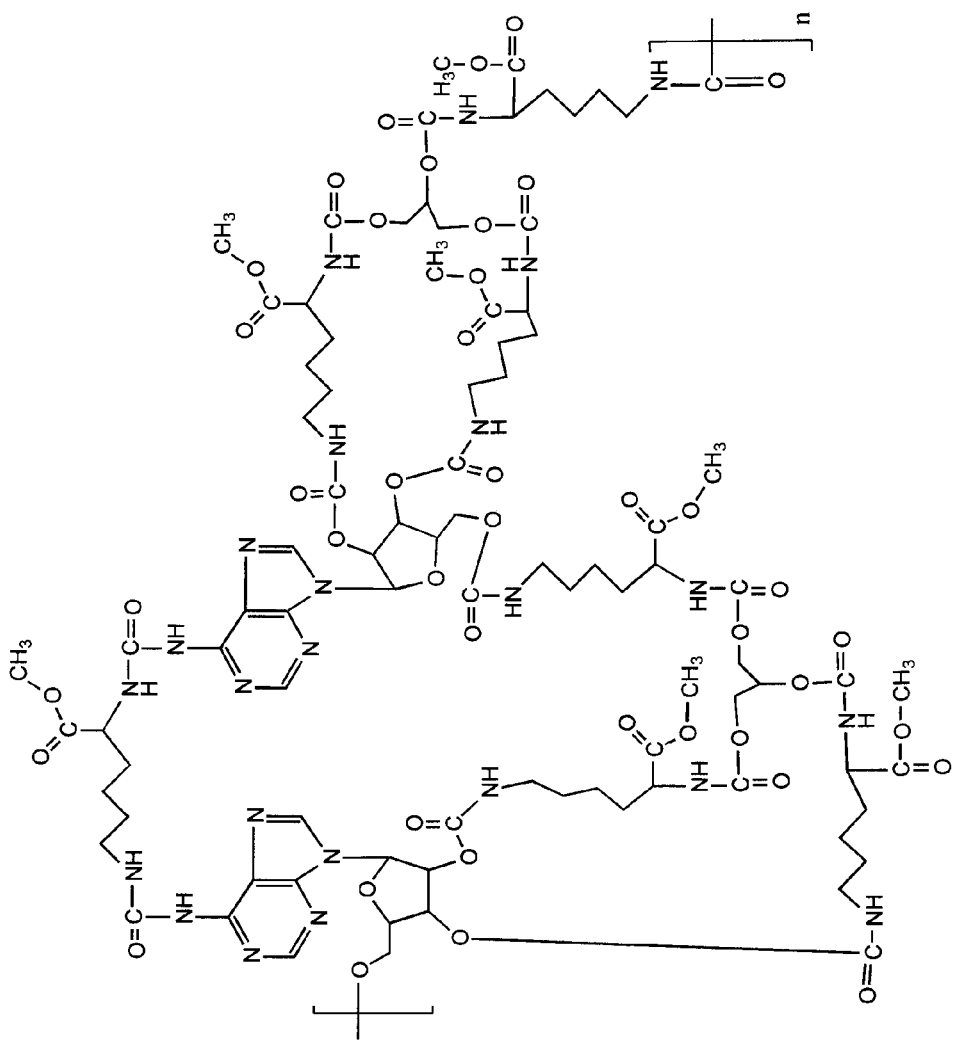
FIG. 7 shows the structure of a specific example of a polymer of adenosine, lysine methyl ester and glycerol.

Wire was cut into small pieces, burnished using sand paper to remove the oxide surface, then washed with distilled water and sterilized by autoclave. The wires were weighted (labeled $W_0$) and immersed first into LDI-Adenosine Monomer to get the first layer coating. Subsequently, the wire was placed in LDI-Glycerol Monomer to get the second layer coating on top of the first layer of coating. The wire was allowed to cure at room temperature overnight to polymerize the two monomers together. This reaction is illustrated in FIG. 5, and results in a polymer of adenosine, lysine methyl ester and glycerol that has the general structure illustrated in FIG. 6. A specific example of an adenosine, lysine methyl ester and glycerol polymer is shown in FIG. 7. The next day, the wire was weighted again (labeled $W_1$). The coating ratio was calculated as follows: Coating ratio (%)=$[(W_1-W_0)/W_0]\times 100\%$ $W_1$ stands for the weight of the wires coated with the polymers and $W_0$ stands for the weight of the nude wires (without polymers), respectively Adenosine was used in the synthesis described in Example 1. However, any analogues of adenosine in which the substitutions do not interfere with the above described synthesis can be employed rather than adenosine per se. An example is 2-chloroadenosine which could be substituted for adenosine in the above described synthesis to produce the corresponding LDI-2-Chloroadenosine Monomer and a polymer of 2-chloroadenosine, lysine methyl ester and glycerol. However, many other adenosine analogues could easily be substituted for adenosine.

Example 2

The purpose of the experiment described under Example 2 was to determine whether the polymer of adenosine, lysine methyl ester and glycerol synthesized in Example 1 with adenosine molecules covalently-linked to the polymer (as described in Example 1) could release adenosine rapidly and for a duration of time required for a typical vascular procedure when the adenosine-containing polymer is coated onto a wire (as described in Example 1) and when the wire is in a physiological salt solution at body temperature and pH to mimic the in vivo environment.

One end of a section of Tygon roller pump tubing (Harvard Apparatus; Holliston, Mass.) was placed in a reservoir containing 10-ml of phosphate-buffered saline (PBS) and the pump tubing was inserted into a digital roller pump (model ISM834A, Ismatec; Glattbrug-Zurich, Switzerland). The other end of the pump tubing was attached to a short section of polyethylene-50 tubing and the end of this tubing was placed in the same reservoir. This arrangement allowed for recirculation of perfusate from the reservoir through the polyethylene tubing and back to the reservoir. The reservoir was maintained at 37 degrees C. by placing it in a thermostatically-controlled water bath. A 0.5 cm length of wire (diameter=0.2 mm before coating) coated with the polymer (diameter of wire after coating was less than 1 mm) to which adenosine molecules were covalently linked (as described in Example 1) was inserted through the wall of the polyethylene-50 tubing so that the wire was in the lumen of the tubing and in contact with the PBS. PBS was perfused at 5 ml/min through the polyethylene-50 tubing in a recirculating fashion with the roller pump. At 10-minute intervals, 200 microliters of PBS was removed from the reservoir, and this volume was replaced with the same volume of fresh PBS.

Figure 8:
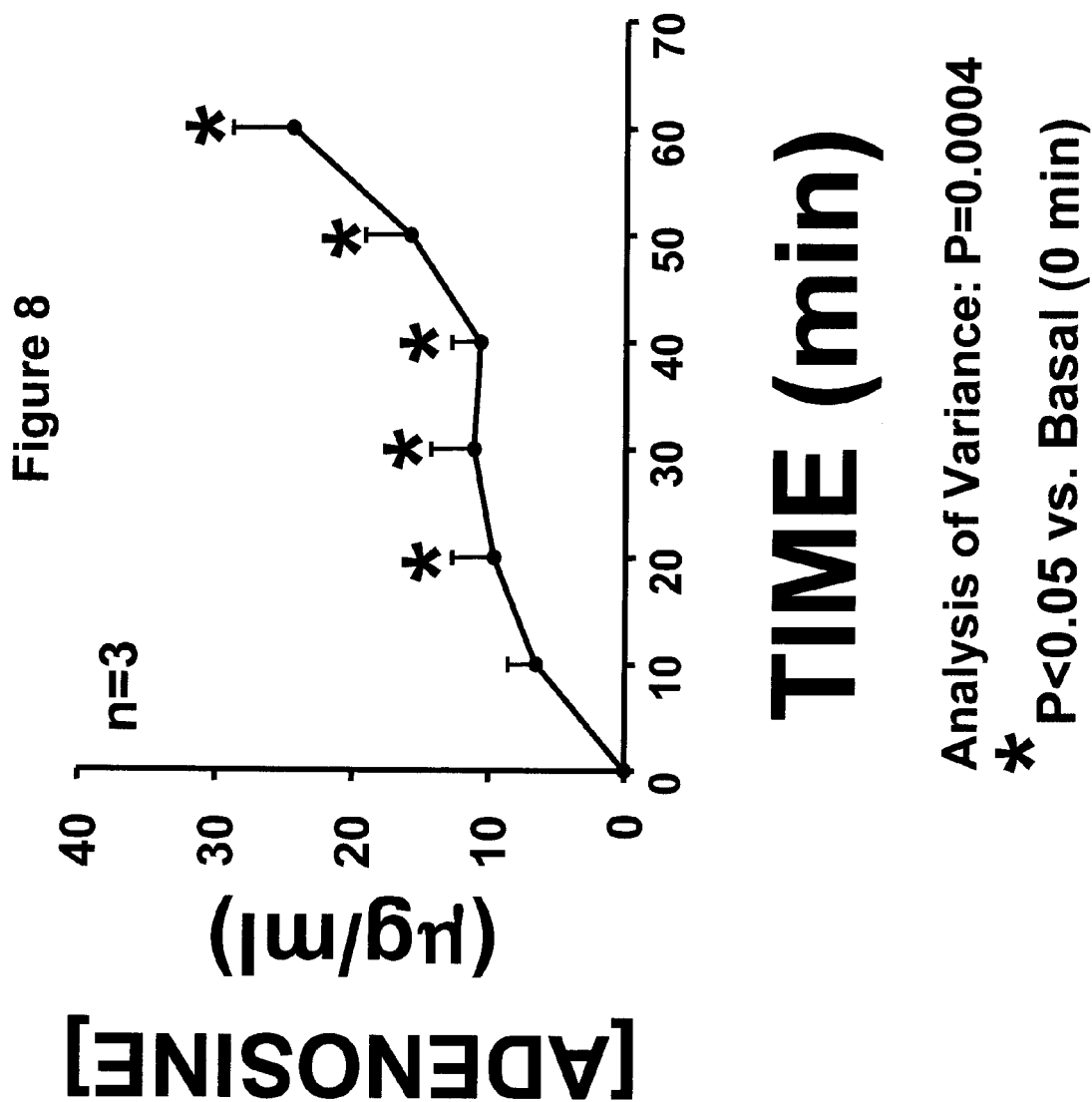
FIG. 8 shows a line graph illustrating the time-related release of adenosine from a wire coated with a polymer of adenosine, lysine methyl ester and glycerol which has adenosine molecules covalently linked to the polymer. A recirculating system pumped phosphate-buffered saline (physiological pH and temperature) from a reservoir, through a tubing and back to the reservoir. The wire coated with the adenosine-containing polymer was inserted into the inline tubing, and samples of phosphate-buffered saline were taken periodically from the reservoir and analyzed for adenosine concentration by liquid chromatography-mass spectrometry. Data were analyzed by analysis of variance followed by a Fisher's Least Significant Difference test.

This procedure was repeated for one hour (6 samples were taken). The concentration of adenosine in the samples was measured using liquid chromatography-mass spectrometry as described previously in detail (see Jackson et al., Journal of Pharmacology and Experimental Therapeutics, 317: 1219 (2006)). As illustrated in FIG. 8, insertion of wire coated with the adenosine-containing polymer caused a significant and time-related accumulation of adenosine in the PBS. FIG. 8 shows that the release of adenosine from the wire coated with the adenosine-containing polymer occurred very rapidly, with significant release during the first 10 minutes and additional release occurring during the subsequent 50 minutes. Thus the covalent bonds linking adenosine to the polymer were non-enzymatically hydrolyzed from the polymer and free adenosine was released into the PBS with a kinetic profile consistent with a rapid release followed by a more sustained release for a duration similar to that used in an ordinary vascular interventional procedure. This experiment shows that the adenosine-containing polymer described in Example 1 can release free adenosine with the appropriate kinetics for treatment/prevention of the no-reflow phenomenon when the polymer is coated on a wire and when this polymer-coated wire comes in contact with water under physiological conditions of temperature and pH.

Example 3

Figure 9:
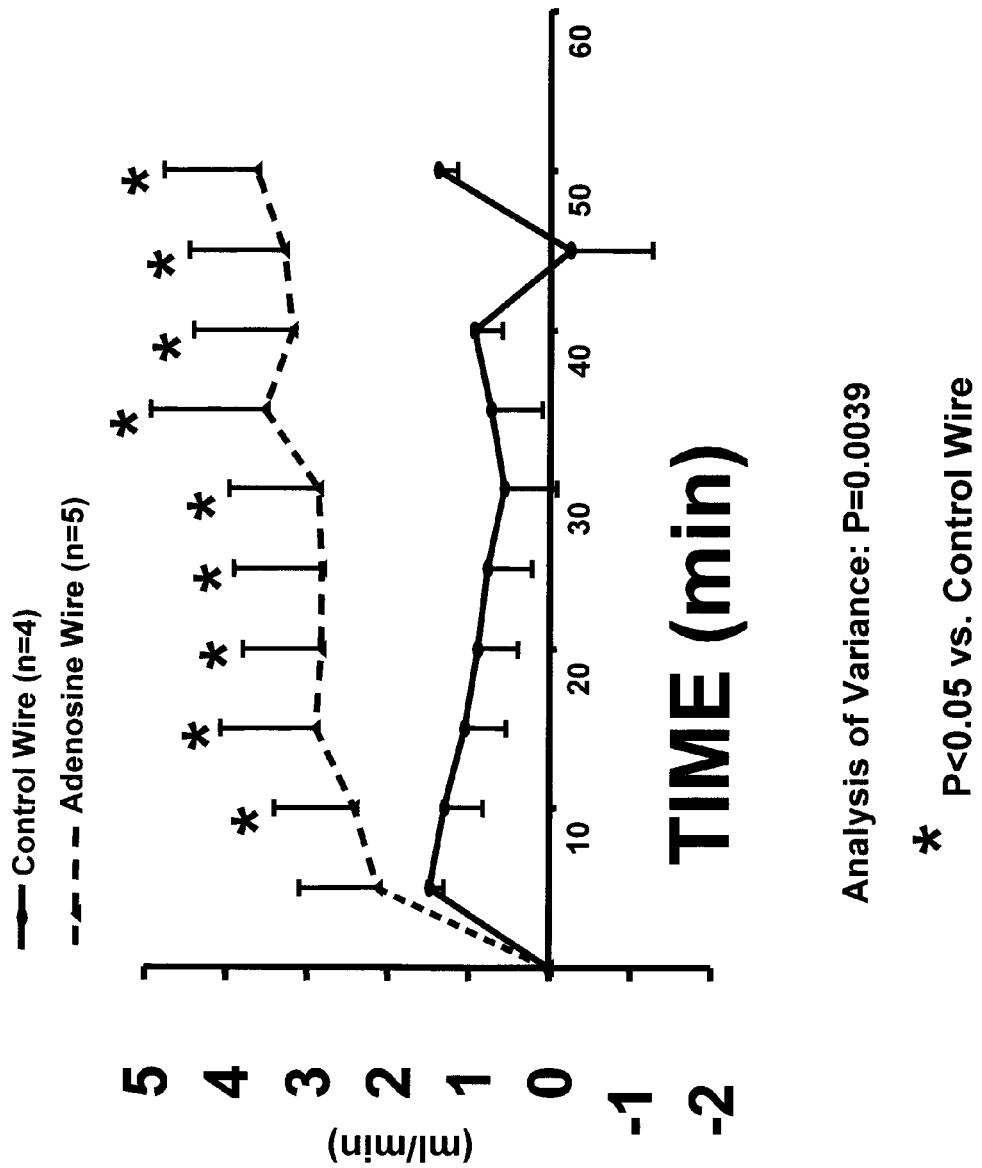
FIG. 9 shows a line graph illustrating the effects of an adenosine-releasing wire (a wire coated with a polymer that has adenosine molecules covalently linked to the polymer in the form of an adenosine, lysine methyl ester and glycerol polymer) or a control wire (a wire coated with a monomer not containing adenosine, i.e., the LDI-Glycerol Monomer) on changes in mesenteric blood flow (MBF) with respect to time. Rats were anesthetized, and the distal aorta was ligated as were both renal arteries. A transit-time flow probe was placed around the superior mesenteric artery and connected to a transit-time flow meter. A 30-gauge needle was placed in the superior mesenteric artery and both methoxamine (3 μg/minute) and angiotensin II (3 ng/minute) were infused into the superior mesenteric artery to cause intense vasoconstriction (increased vascular tone) to mimic the no-reflow phenomenon. The wires were inserted into the aorta just past the ligation and at the level of the superior mesenteric artery. Data were analyzed by analysis of variance followed by a Fisher's Least Significant Difference test.

The purpose of the experiment described under Example 3 was to determine whether the polymer with adenosine molecules covalently-linked to the polymer (as described in Example 1) could release adenosine in pharmacologically-active amounts that counteract the no-reflow phenomenon when the adenosine-containing polymer is coated onto a wire and when the wire is placed in an artery in vivo with blood flowing through the artery. Adult Sprague-Dawley rats were anesthetized with Inactin (90 mg/kg, intraperitoneal injection) and placed on a Deltaphase Isothermal Pad (Braintree Scientific, Inc.; Braintree, Mass.). Body temperature was monitored with a digital rectal probe thermometer (Physiotemp Instruments, Inc.; Clifton, N.J.) and maintained at 37 degrees C. by adjusting a heat lamp above the animal. A polyethylene-240 cannula was inserted into the trachea to facilitate respiration, and a polyethylene-50 cannula was inserted into the carotid artery to monitor arterial blood pressure and heart rate with a digital blood pressure analyzer (Micro-Med, Inc.; Louisville, Ky.). Both renal arteries were ligated and the abdominal aorta below the mesenteric artery was ligated so that all blood flowing into the abdominal aorta at the level of the mesenteric artery was directed into the mesenteric artery. The mesenteric artery was dissected away from the surrounding tissue, a 30 gauge needle connected to a syringe via a polyethylene-10 tubing was inserted into the mesenteric artery, and an infusion of saline (0.9%) at 25 µl/min was initiated into the mesenteric artery by placing the syringe in an syringe pump (Braintree Scientific, Inc.). The blood flow rate (ml/minute) was measured with a transit-time flow probe (Transonic Systems, Inc.; Ithaca, N.Y.) placed around the mesenteric artery and connected to a transit-time flow meter (Transonic Systems, Inc.). After a 30-minute rest period, methoxamine (3 µg/minute) and angiotensin II (3 ng/minute) were infused simultaneously into the mesenteric artery by placing these substances in the syringe that was infusing saline into the mesenteric artery. Methoxamine is a sympathomimetic agent that like endogenous norepinephrine causes intense vasoconstriction by activating vascular $\alpha_1$-adrenoceptors as occurs in vivo during vascular procedures. Angiotensin II is an endogenous peptide that causes intense vasoconstriction by activating vascular $AT_1$ receptors as occurs in vivo during vascular procedures. The purpose of infusing methoxamine and angiotensin II into the mesenteric artery was to cause intense vasoconstriction of the mesenteric vascular bed and thereby reduce mesenteric blood flow and mimic the no-reflow phenomenon. This method was previously validated as a model of intense vasoconstriction of the mesenteric vascular bed (see Jackson et al., Alimentary Pharmacology & Therapeutics 14: 1371 (2000)). After another 30-minute rest period, a 0.5 cm length of wire (diameter=0.008 inches or 0.02 cm before coating) coated with a polymer (final diameter of wire after coating was less than 1 mm) to which adenosine molecules were covalently linked (see Example 1) was inserted into aorta at the level of mesenteric artery (Adenosine Wire Group). In some animals, the wire was coated only with the LDI-Glycerol Monomer without adenosine covalently linked to the polymer (Control Wire Group). Mesenteric blood flow was recorded every five minutes for 50 minutes. As shown in FIG. 9, in the animals in which the wire inserted into the aorta at the level of the mesenteric artery was not coated with the adenosine-containing polymer, there was very little change in mesenteric blood flow over the observation period. In contrast, in the animals in which the wire inserted into the aorta at the level of the mesenteric artery was coated with the adenosine-containing polymer, mesenteric blood flow increased immediately and the increase was sustained for the duration of the vascular procedure. There was a statistically significant difference in the change in mesenteric blood flow induced by the wire coated with the adenosine-containing polymer versus the wire not coated with the adenosine-containing polymer (FIG. 9).

Example 4

Many medical devices are metallic and therefore are candidates for coating using an electro-polymerization method that would provide more even, uniform and controlled coating of the surface of the medical device. Example 4 is an example of a novel, biocompatible, biodegradable, adenosine-containing polymer that can be used for electro-polymerization coating of metallic devises including guide wires and stents. Coating thickness, adherence and drug-releasing properties can be controlled by altering current duration and intensity, monomer composition and concentration, solvents, and reaction conditions. Electro-polymerization coating provides a fast and reproducible process to improve the biocompatibility and drug-releasing potentials of medical devices.

The implantation of metallic devices, such as guide wires and stents, is a widely accepted therapy for obstructive coronary artery diseases. A number of techniques for coating metallic medical devices have been developed. Conventionally, the medical device is dipped into a polymer-drug solution which dries to form a film. This method has some significant disadvantages, such as "bridging", pooling and lack of uniformity, making it more difficult for scale-up production processes. Uniform, continuous coating can be achieved by spraying the devices with the polymer solution; however, the resulting thickness may still be greater than what is desired. Alternatively, chemical vapor deposition can achieve uniform coatings of controlled thickness and morphology; however, this requires high temperature and pressure environments and complex equipment (see e.g., Lahann, J. et al., J. Mater. Sci., Mater. Med. 10:443 (1999)).

Although electro-polymerization has been used for the preparation of conducting polymers, very little has been reported on its use for coating implantable, metallic medical devices. Conductive properties of the metal substances in which they are manufactured make guide wires and stents suitable candidates for electro-polymerization.

Example 4 describes the design and synthesis of a new adenosine-containing polymer for deposition on metallic surfaces of medical devices, including guide wire and stent surfaces, by a simple one-step electro-polymerization coating process.

Lysine diisocyanate methyl ester (LDI) was purchased from Chemical Division, Kyowa Hakko Kogyo Co. Ltd. (Tokyo, Japan). All other reagents were obtained from Aldrich Chemical Co. (Milwaukee, Wis.).

Figure 10:
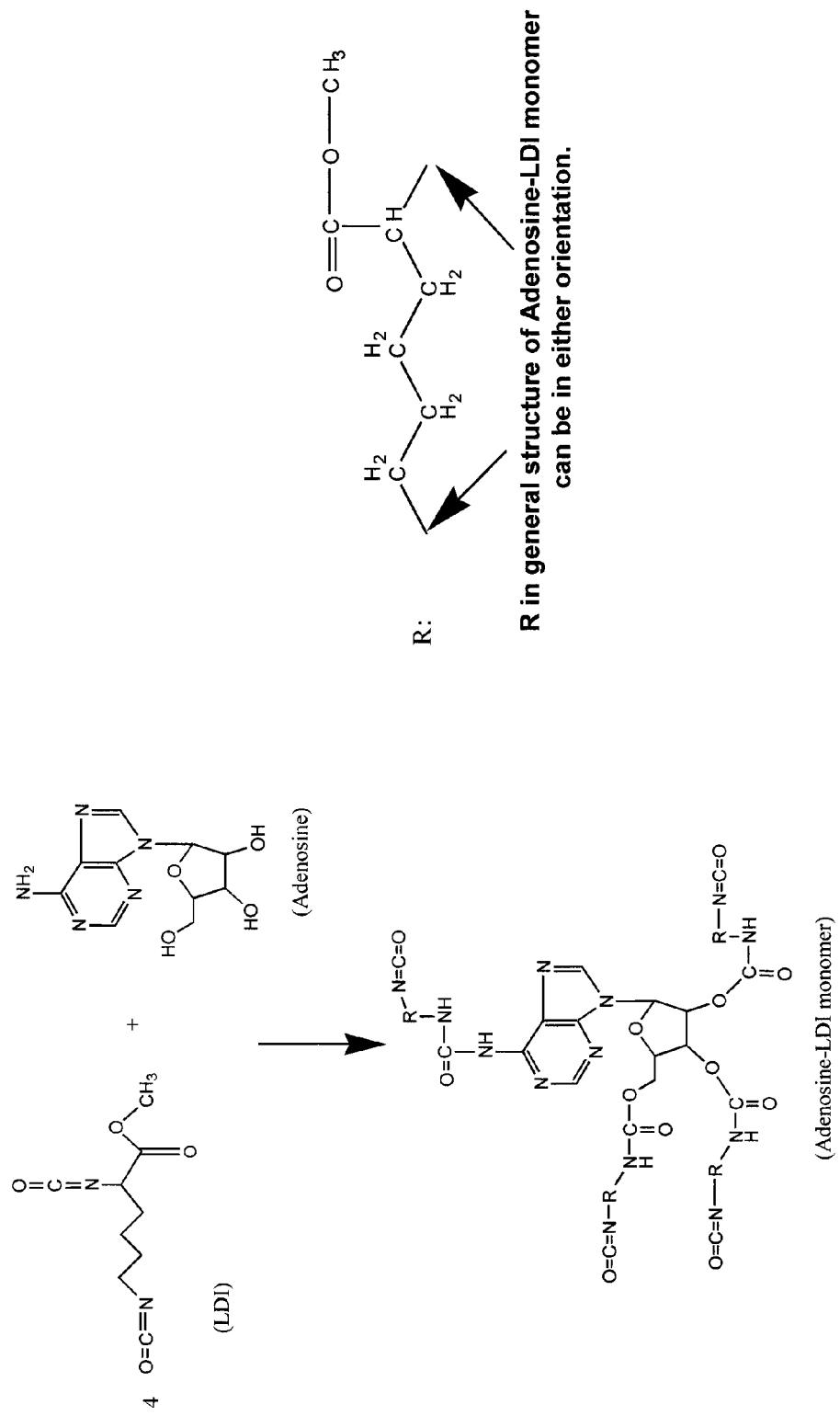
FIG. 10 shows the synthesis of Adenosine-LDI Monomer.
Figure 11:
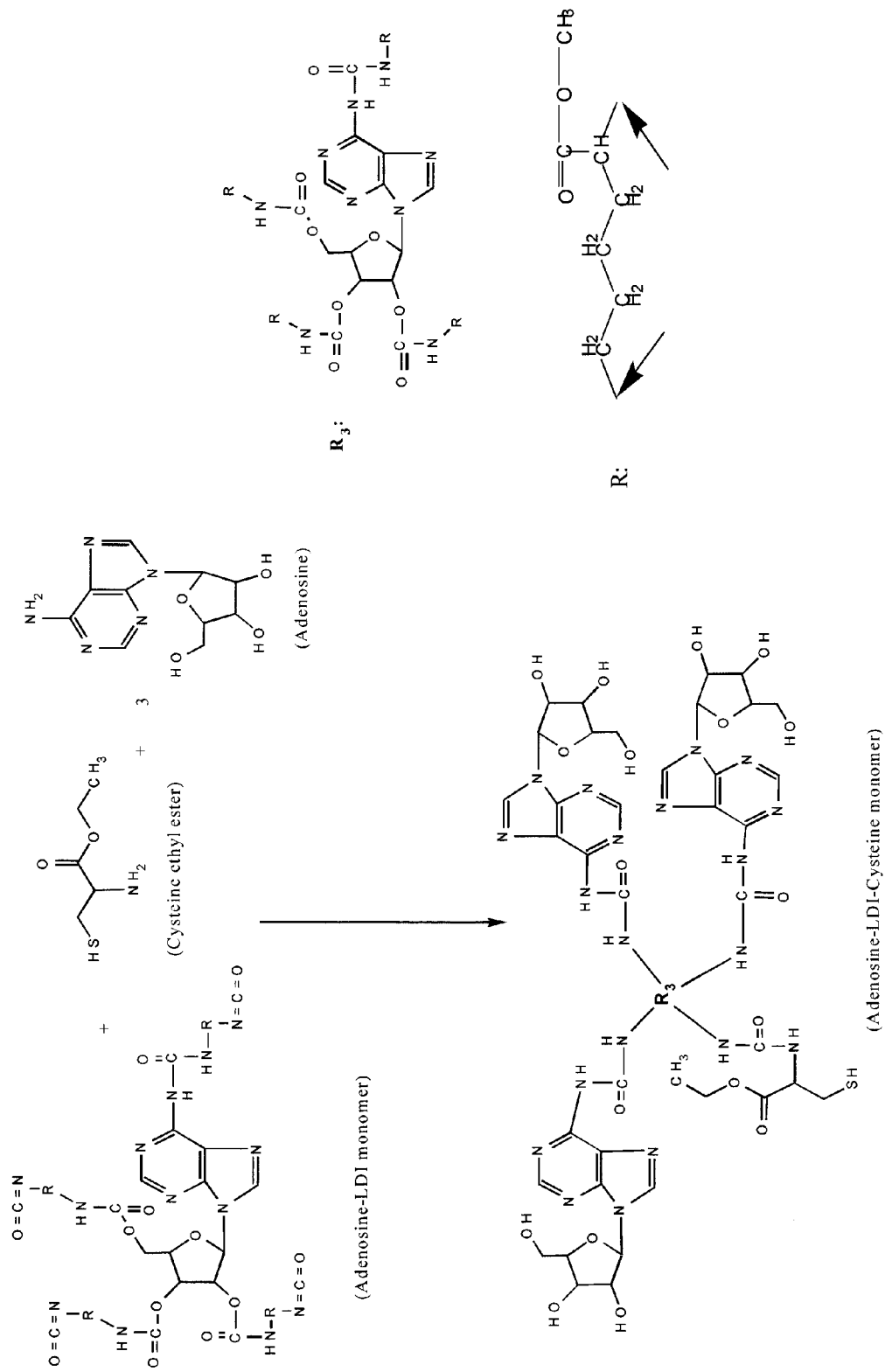
FIG. 11 shows synthesis of Adenosine-LDI-Cysteine Monomer from Adenosine, Adenosine-LDI Monomer and cysteine.
Figure 12:
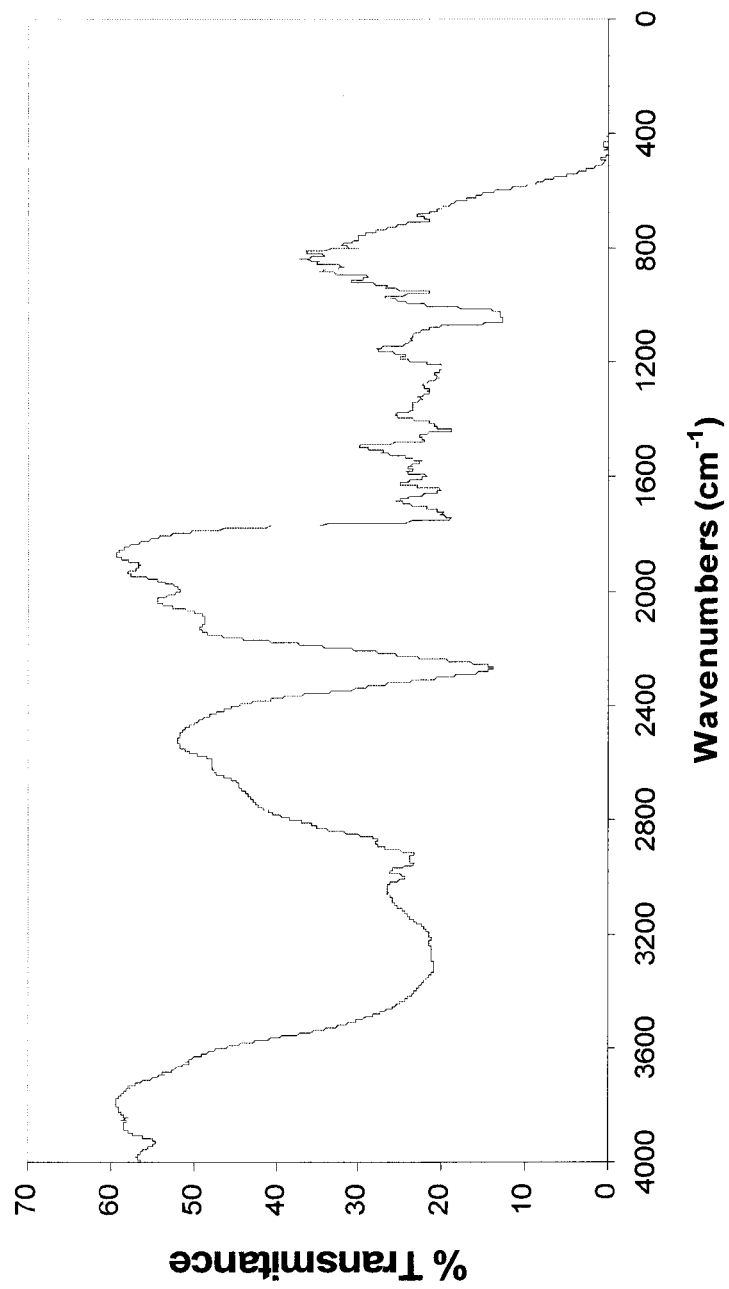
FIG. 12 shows FT-IR spectrum of Adenosine-LDI Monomer.

The monomer for electro-polymerization was synthesized in two steps as shown in FIGS. 10 and 11, respectively. The synthesis of the Adenosine-LDI Monomer (FIG. 10) was accomplished by placing 0.26 g adenosine (MW 267.25, 1 mmol, —$NH_2$ 1 mmol, —OH 3 mmol) and 2 ml of DMSO into a dry round-bottomed flask, flushed with nitrogen and fitted with rubber septa and sealed. Subsequently, 0.85 g of LDI (MW 212, 4 mmol; —NCO 8 mmol) was added into the reaction mixture by a syringe. The reaction mixture was stirred in the dark at room temperature for 2 days. In this first step, the functional groups (hydroxyl and amine groups) of adenosine were capped using LDI (LDI to adenosine molecular ratio of 4 to 1) to produce the isocyanate-terminated monomer shown in FIG. 10. The disappearance of the isocyanate groups and accompanying formation of urethane linkages were monitored by FT-IR. FT-IR spectroscopy is a simple but powerful technique to monitor the formation of carbonyl compounds. As shown in FIG. 12, all function groups of adenosine were covered by isocyanate group, and showed well-defined and strong carbonyl adsorption bands, in a fairly broad wave numbers range of 1610-1760 $cm^{-1}$. The peak maximum of the ester carbonyl was at 1747 $cm^{-1}$. The carbonyl peak of the urethane was at 1658 $cm^{-1}$ and that of the urea was at 1631 $cm^{-1}$. FT-IR spectrum therefore indicated that adenosine had bonded with LDI.

Figure 13:
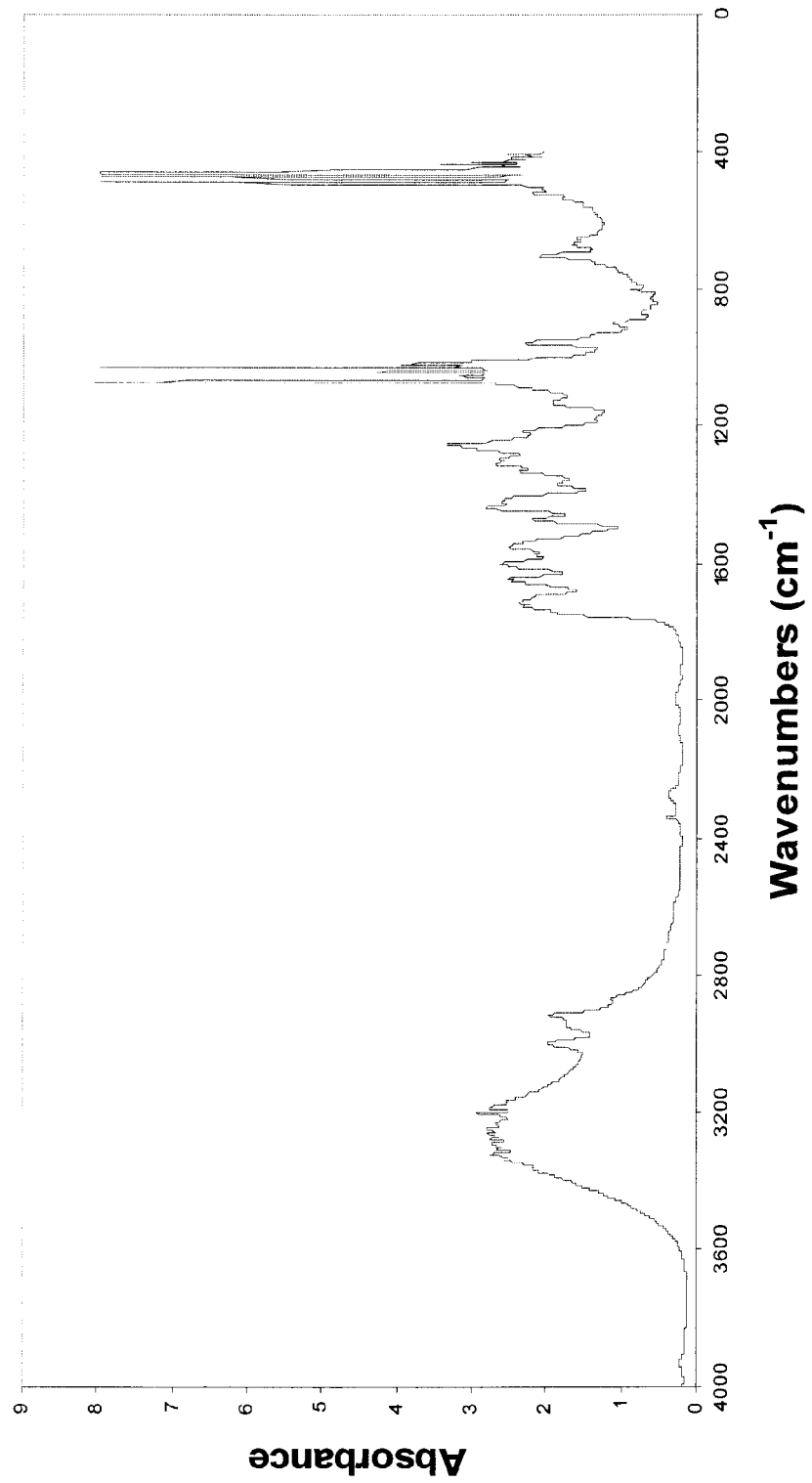
FIG. 13 shows FT-IR spectrum of Adenosine-LDI-Cysteine Monomer.

The second reaction step was started by the addition of adenosine and cysteine ethyl ester hydrochloride. A solution of adenosine (0.8 g, FW 267.25, 3 mmol) and cysteine ethyl ester hydrochloride (0.185 g, 1 mmol) in 5 ml DMSO was added to the reaction mixture when the FT-IR suggested that 50% of isocyanate groups (peak at 2285 $cm^{-1}$) initially present had been consumed. The reaction mixture was then stirred at room temperature for another 2 hours until the FT-IR showed no remaining isocyanate groups (FIG. 13). The synthesis of Adenosine-LDI-Cysteine Monomer (FIG. 11) was confirmed by the appearance of the strong absorption bands at approximately 1610 to 1760 $cm^{-1}$, attributable to the formation of the —NHCOO— and —NHCONH— groups, with the accompanying complete disappearance of the —N=C=O peak at 2285 $cm^{-1}$. The peaks at 1438 and 773 $cm^{-1}$ assigned to C—S stretching bands were also observed, which indicated that cysteine was attached to the Adenosine-LDI Monomer and an Adenosine-LDI-Cysteine Monomer had formed (FIG. 13). Following this two-step synthesis, the reaction solution was ready for use in the electro-polymerization procedure.

Figure 14:
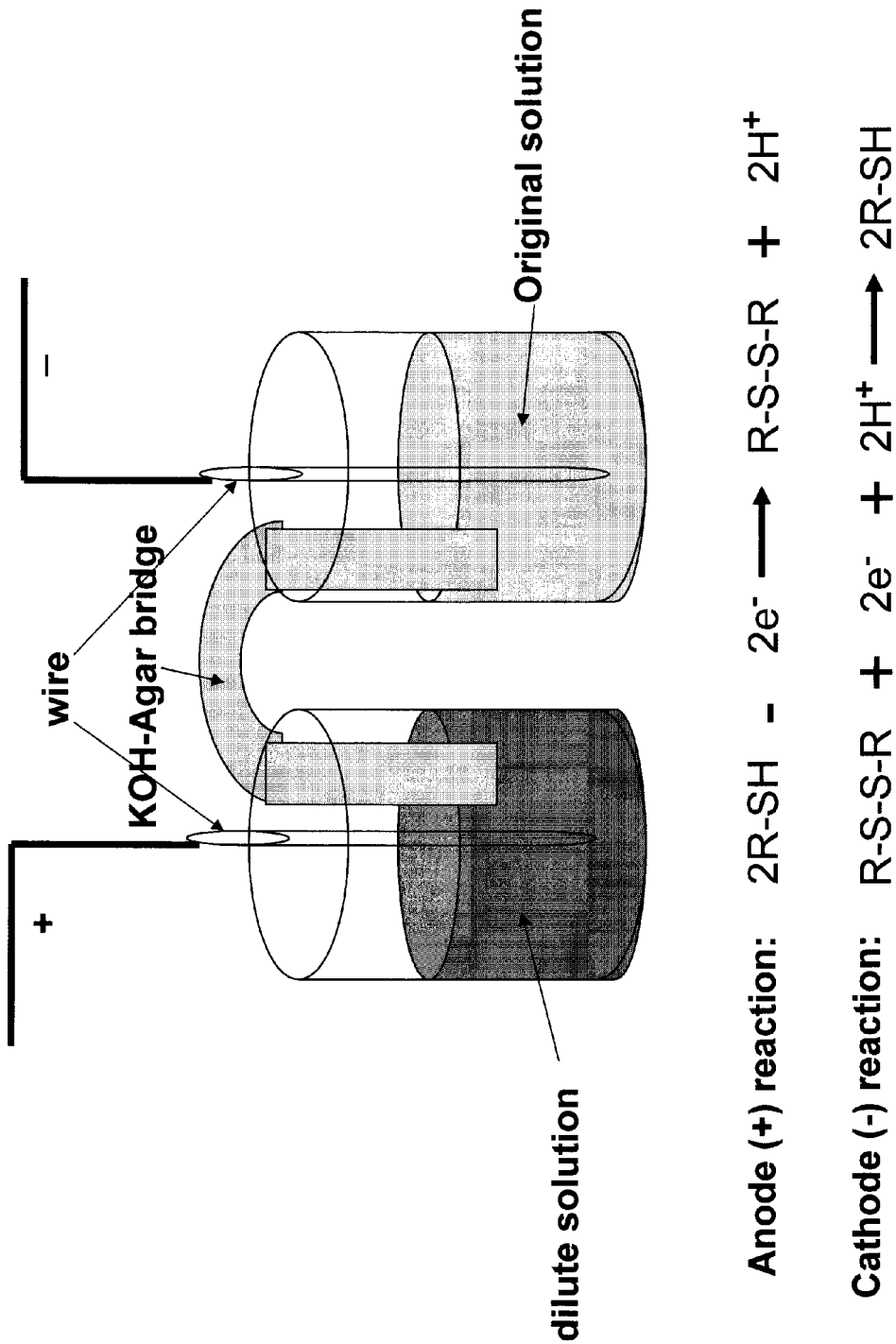
FIG. 14 shows electro-polymerization method of coating wire with polymer of adenosine, lysine methyl ester and cysteine ethyl ester.
Figure 16:
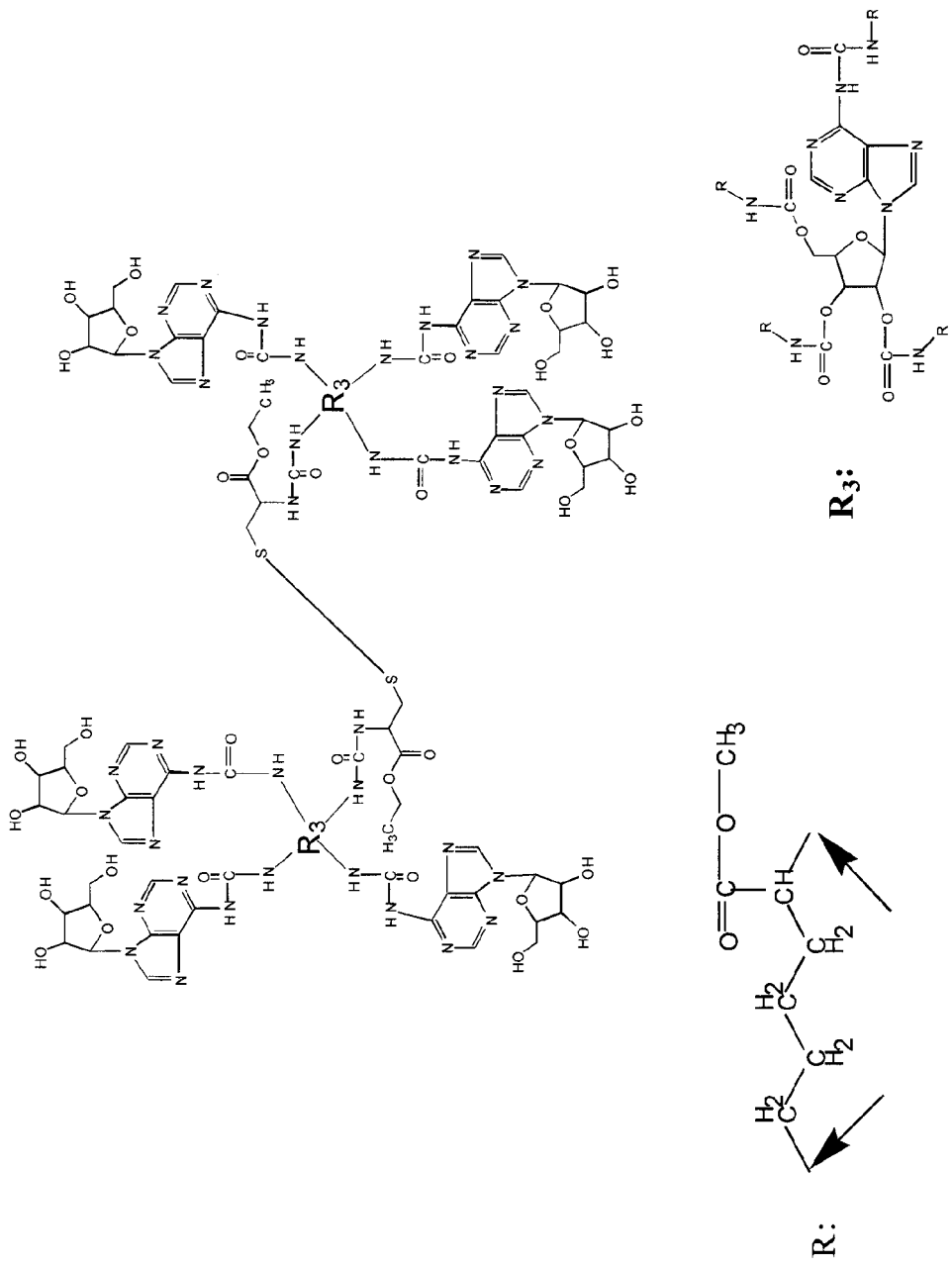
FIG. 16 shows general structure of the polymer of adenosine, lysine methyl ester and cysteine ethyl ester.

Eight grams of the above reaction mixture was used for electro-coating the wires. The method of electro-polymerization is illustrated in FIG. 14. Electro-polymerization was performed by cyclic voltammetry with the anode wire dipped in a diluted solution of the original Adenosine-LDI-Cysteine Monomer reaction solution (3 g of the original Adenosine-LDI-Cysteine Monomer reaction solution with 2 g of DMSO) and the cathode wire dipped in the original solution (5 g). The two vessels containing the diluted and undiluted reaction solution were connected by a KOH-agar bridge (0.5 g agar in 50 ml of 1 M KOH). The electro-polymerization (reaction shown in FIG. 15) occurred on the anode wire surface and a uniform, thin coat of an adenosine-containing polymer (see FIG. 16 for general structure) with defined morphology was obtained at 10 mA current for 10 min. The wire was left at room temperature overnight to dry and weighted again (labeled $W_1$), the coating ratio was calculated as follows, where $W_1$ stands for the weight of the wires coated with the polymer and $W_0$ stands for the weight of the bare wire: Coating ratio (%)=[($W_1-W_0$)/$W_0$]×100%

Figure 17:
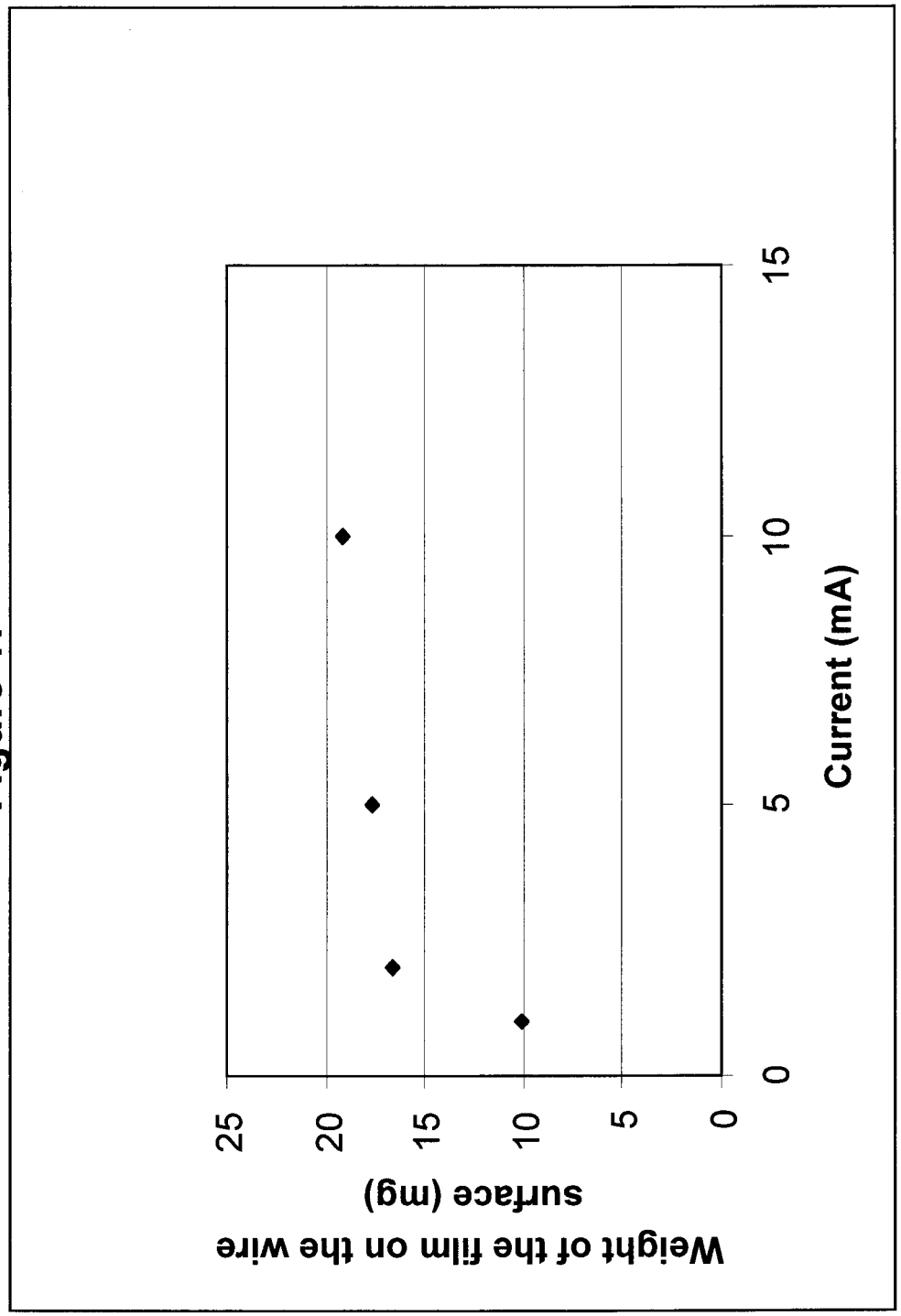
FIG. 17 shows effect of electrical current on deposition of polymer of adenosine, lysine methyl ester and cysteine ethyl ester on wire surface.
Figure 18:
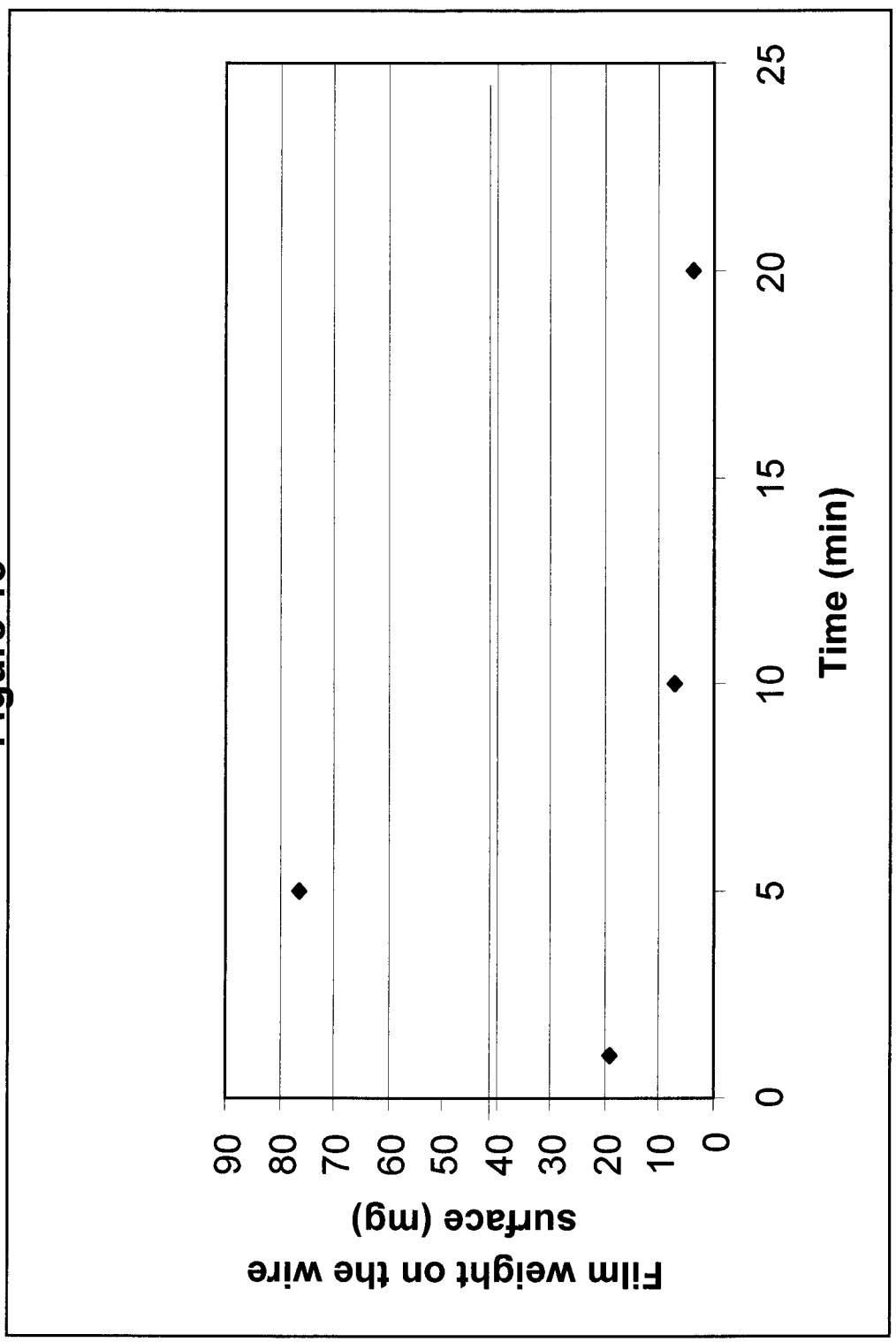
FIG. 18 shows effect of time on deposition of polymer of adenosine, lysine methyl ester and cysteine ethyl ester on wire surface.

Wires (either copper or guide wires) were coated with an adenosine-containing polymer by electro-polymerization as described above. A continuous and homogenous film was deposited on the wire surface. The speed and thickness of coating increased with amperage. As shown in FIG. 17, about 10 mg of polymer deposited on the surface of a copper wire exposed to 1 mA current for 1 min. More than 19 mg of polymer was coated on the wire surface supplied with 10 mA current for 1 min (FIG. 17). Polymer deposition on the wire surface increased with time under the same current during the first 5 min (FIG. 18). Subsequently, the weight of polymer coated on the wire surface decreased and a shell of the polymer film was observed around the wire. This can be explained by the diameter of the wire being too small to carry enough polymer film.

Figure 19:
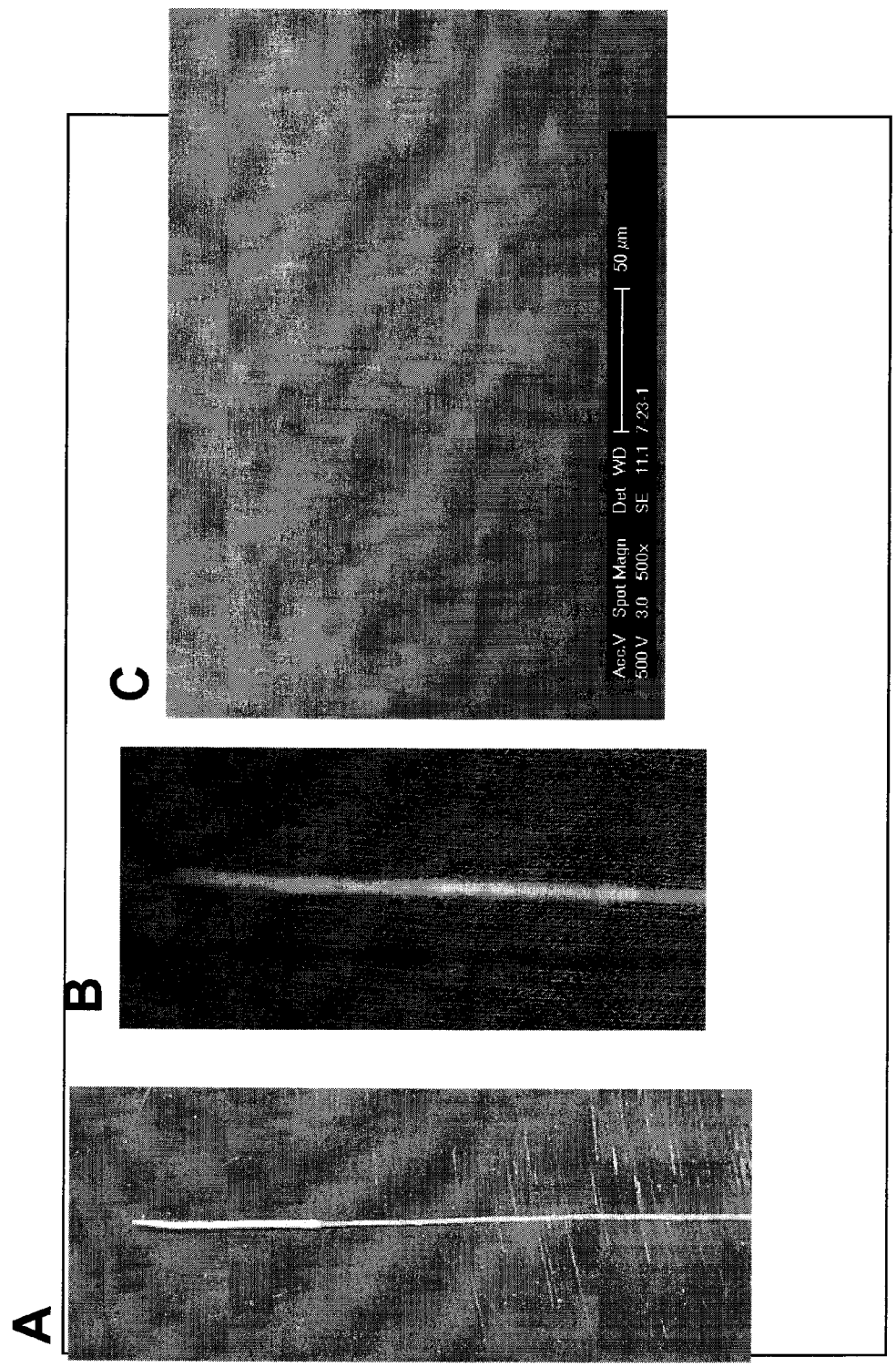
FIG. 19 shows morphology of coating of polymer of adenosine, lysine methyl ester and cysteine ethyl ester on copper wire surface. The surface of the wire was coated by electro-polymerization process using 1 mA for 2 min. Panels A and B show that a smooth film was coated on the wire surface. Panel C shows surface using a scanning electron micrograph of the same sample (magnification=500×).

Morphology of the electro-polymerization coating with the adenosine-containing polymer was investigated by scanning electronic microscopy (SEM). FIG. 19 shows the morphology of a copper wire coated with the polymer of adenosine, lysine methyl ester and cysteine ethyl ester under 10 mA current for 2 min. FIG. 20 shows the morphology of a guide wire (HI-TORQUE Guide wires; Guidant Corporation; Santa Clara, Calif., USA) coated by the same polymer under the same conditions. As shown in FIGS. 19 and 20, the film was continuous and smooth, exhibiting a uniform thickness over the whole film. Further, from the scanning electron micrograph of the wire surface, the film displayed an amorphous surface features at lower magnification. Our experiments indicated that the functional surface of the guide wires can be controlled by the composition and properties of the monomers, dopant anion, temperature, pH and solvent during the electro-polymerization coating process.

Adenosine was used in the synthesis described in Example 4. However, any analogue of adenosine in which the substitutions do not interfere with the above described synthesis can be employed rather than adenosine per se. An example is 2-chloroadenosine which could be substituted for adenosine in the above described synthesis to produce the corresponding 2-Chloroadenosine-LDI-Cysteine Monomer and a polymer of 2-chloroadenosine, lysine methyl ester and glycerol.

Example 5

In this first step of Example 4, the function groups (hydroxyl and amine groups) of adenosine were capped using LDI (LDI to adenosine molecular ratio of 4 to 1) to produce the isocyanate-terminated monomer shown in FIG. 10. In Example 4, the second reaction step was started by the addition of adenosine and cysteine ethyl ester hydrochloride. However, this reaction may easily be modified by omitting cysteine ethyl ester hydrochloride and increasing the amount of adenosine added such that four moles of adenosine are added per mole of Adenosine-LDI monomer. This reaction yields the product shown in FIG. 21, which is the Pentameric Adenosine-LDI Monomer. However, any analogues of adenosine in which the substitutions do not interfere with the above described synthesis can be employed rather than adenosine per se. An example is 2-chloroadenosine which could be substituted for adenosine in the above described synthesis to produce the corresponding 2-Chloroadenosine-LDI Monomer.

Example 6

Figure 21:
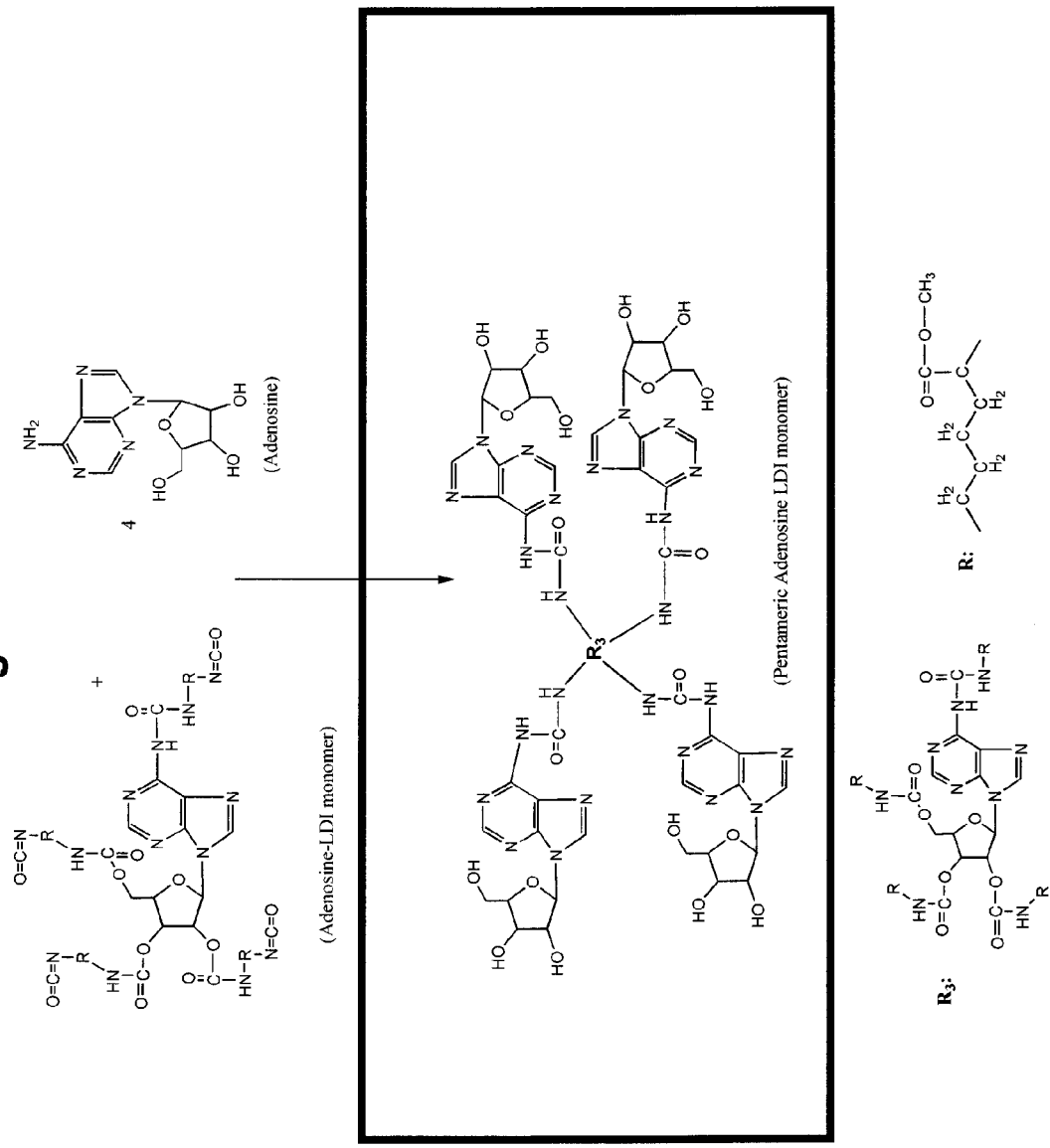
FIG. 21 shows the synthesis of the Pentameric Adenosine-LDI Monomer.
Figure 22:
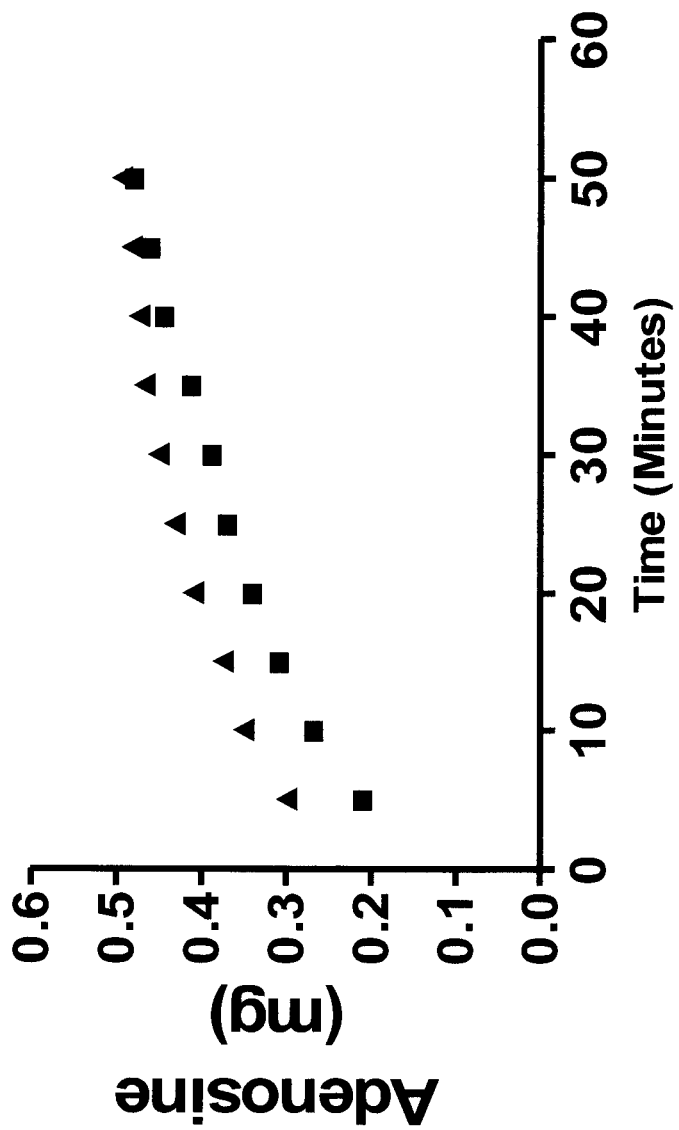
FIG. 22 shows a graph illustrating the time-related release of adenosine from the tip of two separate cardiac guide wires coated with a monomer of adenosine (LDI-Adenosine Monomer; see chemical structure in FIG. 4) with free adenosine molecules added to the monomer solution during wire coating. The cardiac guide wire tip was briefly dipped into the monomer solution containing excess free adenosine, removed and then dried rapidly with a warm air stream. This procedure was repeated until the wire was evenly coated with about 1 mg of adenosine. The guide wire tip coated with the adenosine monomer/free adenosine mixture was then gently placed into a beaker containing phosphate-buffered saline at 37° C. that was constantly stirred with a magnetic device. Samples were taken periodically from the beaker and analyzed for adenosine amount by UV spectrophotometry (absorption at 260 nm).

Monomers containing two are more molecules of adenosine, such as described in FIG. 4 (LDI-Adenosine Monomer) and FIG. 21 (Pentameric Adenosine-LDI Monomer) can be used to release adenosine from medical devices, such as guide wires, without further polymerization. This can be accomplished either with or without addition of free adenosine molecules or free molecules of adenosine analogues to the coating solution of the monomer. For the purposes of this disclosure, the term "free" indicates molecules of adenosine or adenosine analogues that are not covalently linked to a monomer or polymer, but are entrapped in the composition as a mixture. FIG. 22 shows a graph illustrating the time-related release of adenosine from the tip of two separate cardiac guide wires coated with a monomer of adenosine (LDI-Adenosine Monomer; see chemical structure in FIG. 4) with free adenosine molecules added to the monomer solution during wire coating. The cardiac guide wire tip was briefly dipped into the monomer solution containing excess free adenosine, removed and then dried rapidly with a warm air stream. This procedure was repeated until the wire was evenly coated with about 1 mg of adenosine. The guide wire tip coated with the adenosine monomer/free adenosine mixture was then gently placed into a beaker containing phosphate-buffered saline at 37° C. that was constantly stirred with a magnetic device. Samples were taken periodically from the beaker and analyzed for adenosine amount by UV spectrophotometry (absorption at 260 nm). A time-related release of adenosine was then observed.

What is claimed is:

1. A medical device for attenuating no-reflow phenomenon, comprising
   a cardiac guide wire;
   a polymer or a monomer formed from a polyisocyanate and adenosine, coating at least a portion of the wire; and
   optionally, free adenosine, not covalently linked to the polymer or the monomer, but entrapped in the polymer or monomer,
   wherein the polymer or monomer is configured to release adenosine to the blood vessels upon contact between the polymer or monomer and a body fluid, thus causing dilation of blood vessels within five minutes of release.

2. The medical device of claim 1 wherein the polymer is formed by the reaction of:
   a monomer formed by reacting a polyisocyanate with a polyol,
   with a monomer formed by reacting a polyisocyanate with adenosine.

3. The medical device of claim 1 wherein the polyisocyanate is lysine diisocyanate or a lysine diisocyanate ester.

4. The medical device of claim 1 wherein the polymer or a monomer is formed by reacting a polyisocyanate, a polyol, and adenosine.

5. The medical device of claim 1 wherein the polymer or monomer is formed by reacting adenosine, lysine diisocyanate or a lysine diisocyanate ester, and glycerol.

6. The medical device of claim 1, wherein the polymer comprises units of the formula (I):

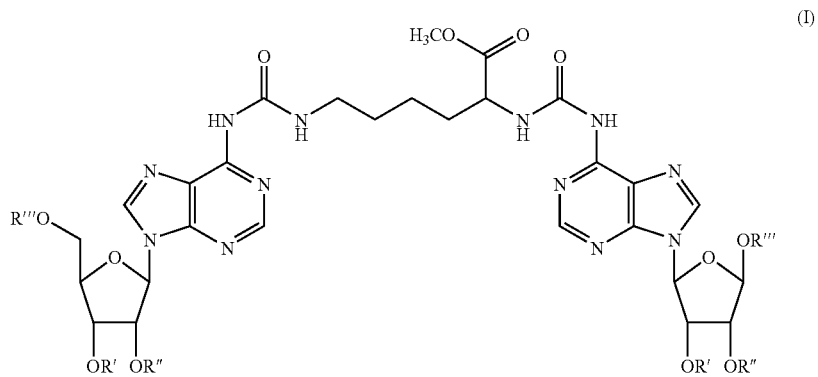

wherein R', R", and R'" represent the same or a different unit having the formula (II):

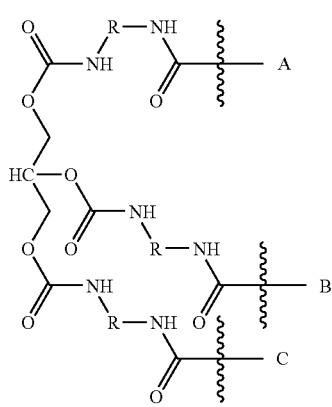

such that the unit of formula (II) can bond to formula (I) through any combination of the bonding sites A, B, and C; and each R is independently a unit having the formula:

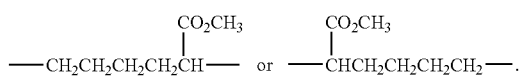

7. The medical device of claim 1 wherein the polymer comprises a monomer having the formula:

wherein each R unit is independently selected from a unit having the formula:

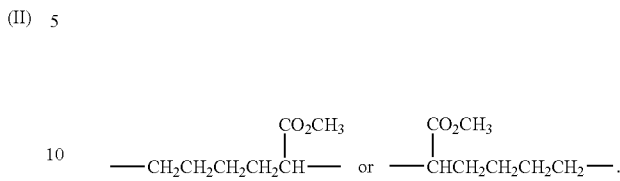

8. The medical device of claim 1 wherein the polymer comprises a monomer having the formula:

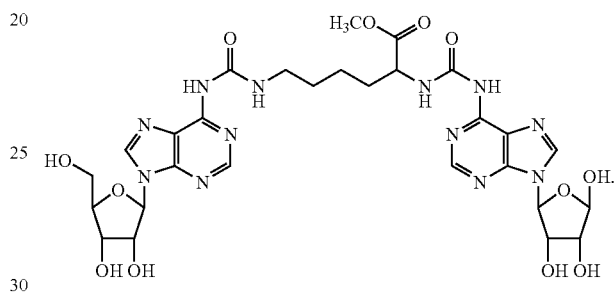

(IV)

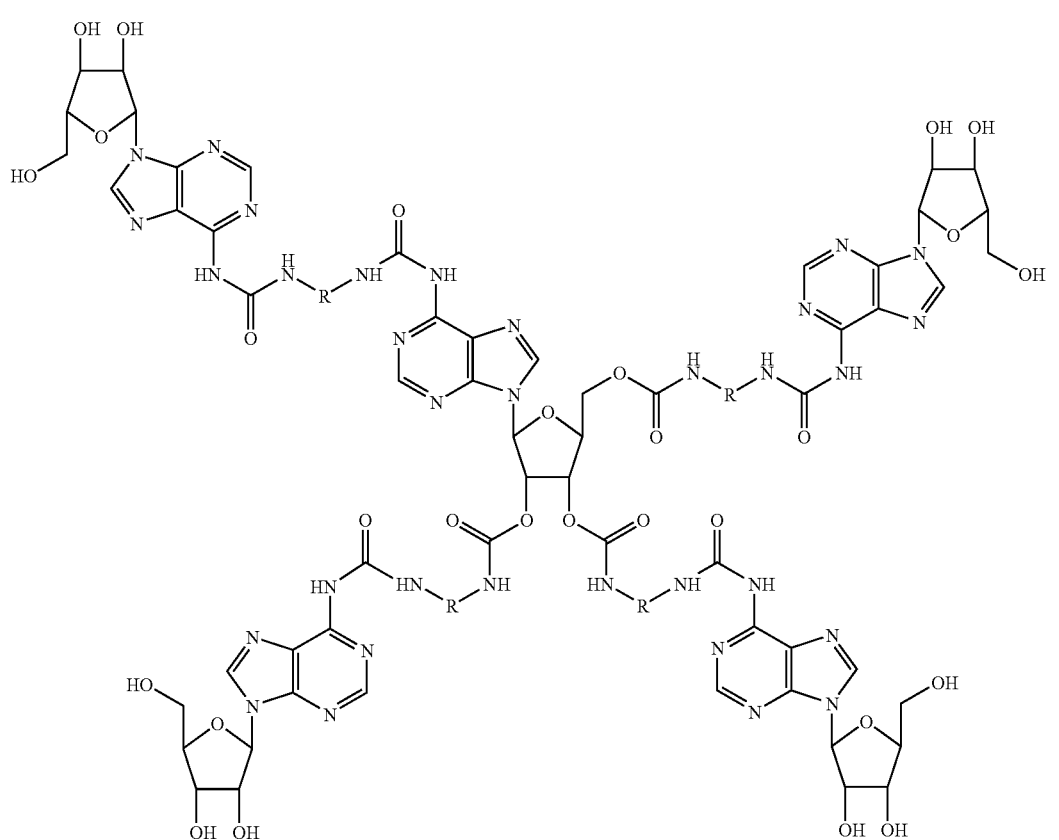

9. The medical device of claim 1 wherein the polymer comprises the formula:

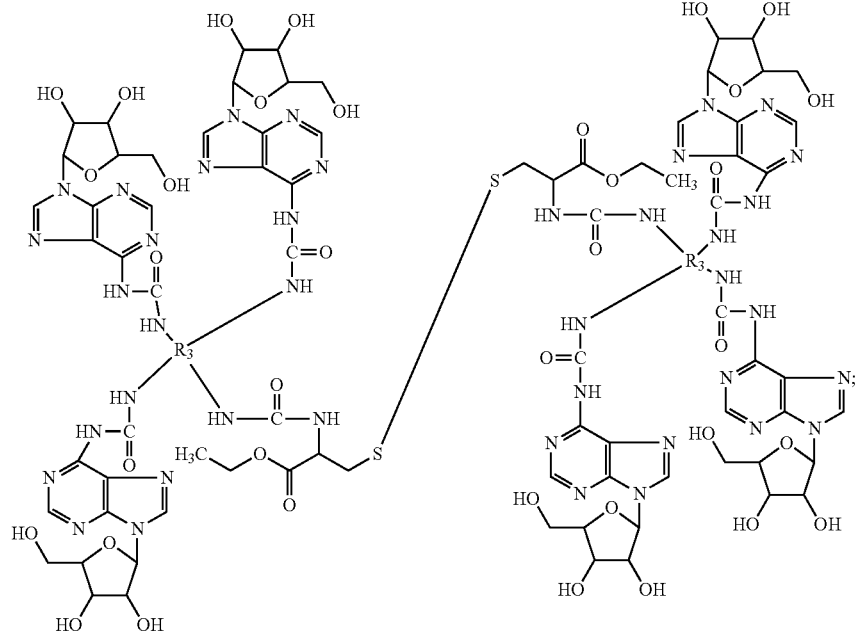

wherein $R_3$ has the formula:

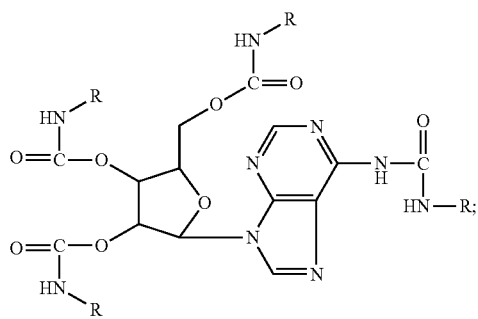

and wherein each R is independently a unit having the formula:

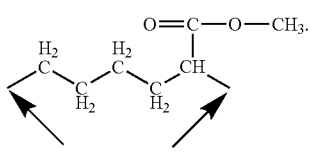

10. A medical device for attenuating no-reflow phenomenon, comprising a cardiac guide wire, wherein at least a portion of the wire is coated with a polymer formed by the reaction of an LDI-Adenosine monomer with an LDI-Glycerol monomer, wherein the device is configured to release adenosine to the blood vessels upon contact with a body fluid, thus causing dilation of blood vessels.

11. The medical device of claim 10, further comprising free adenosine, not covalently linked to monomer or polymer, but entrapped in the polymer.

12. The medical device of claim 10, wherein the LDI-Adenosine monomer has the formula:

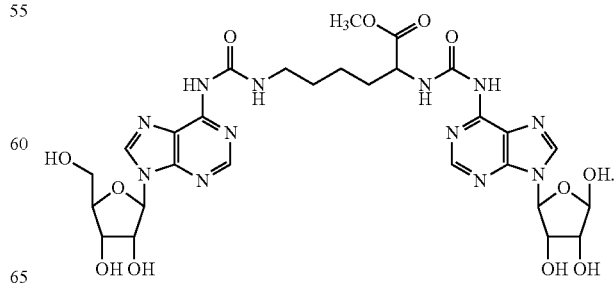

13. The medical device of claim 10, wherein the LDI-Glycerol monomer has the formula:

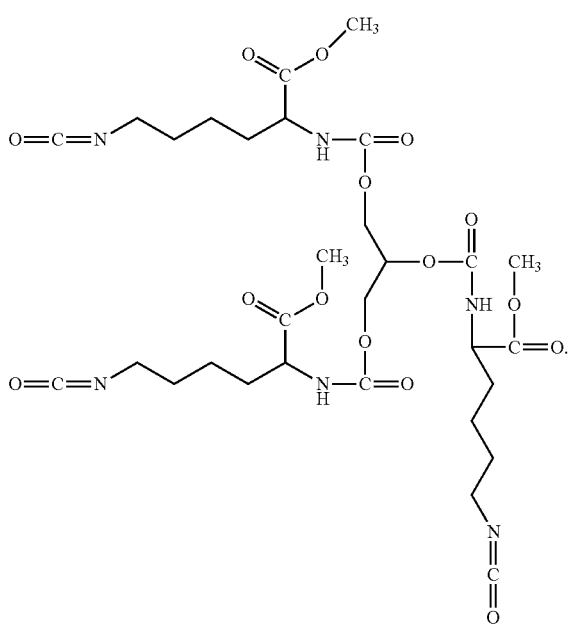 [SMILES: COC(=O)C(CCCCN=C=O)NC(=O)OCC(COC(=O)NC(CCCCN=C=O)C(=O)OC)OC(=O)NC(CCCCN=C=O)C(=O)OC]

14. The medical device of claim 10 wherein the LDI-Glycerol monomer is provided by reaction of glycerol with excess lysine diisocyanate or a lysine diisocyanate ester.

15. The medical device of claim 10, wherein the LDI-Adenosine monomer is provided by reaction of excess adenosine with lysine diisocyanate or a lysine diisocyanate ester.

16. A medical device for attenuating no-reflow phenomenon, comprising a cardiac guide wire, wherein at least a portion of the wire is coated with a polymer formed by polymerization of an Adenosine-LDI-Cysteine monomer, wherein the device is configured to release adenosine to the blood vessels upon contact with a body fluid, thus causing dilation of blood vessels.

17. The medical device of claim 16, further comprising free adenosine, not covalently linked to monomer or polymer, but entrapped in the polymer.

18. The medical device of claim 16, wherein the Adenosine-LDI-Cysteine monomer is provided by reaction of an Adenosine-LDI monomer with a cysteine ester and excess adenosine.

19. The medical device of claim 18, wherein the LDI-Adenosine monomer is provided by reaction of excess lysine diisocyanate or a lysine diisocyanate ester with adenosine.

20. The medical device of claim 18, wherein the LDI-Adenosine monomer has the formula:

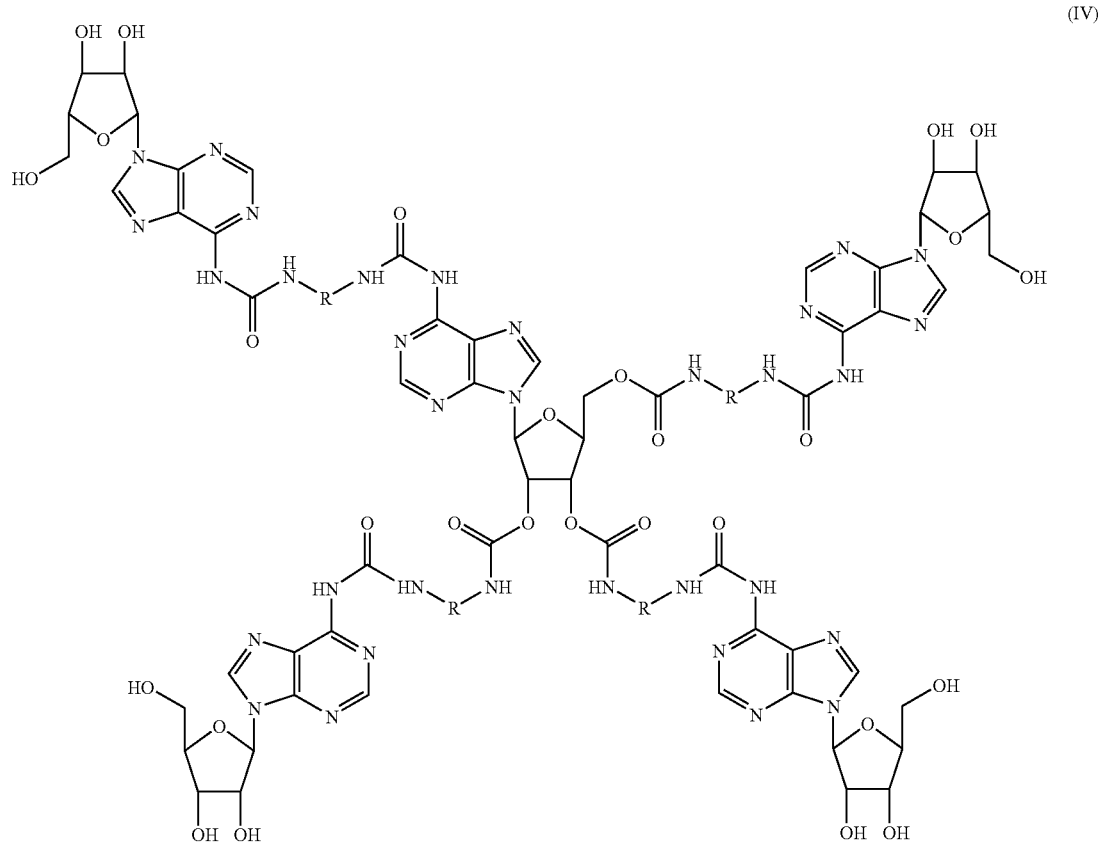

(IV)

21. The medical device of claim 16, wherein the Adenosine-LDI-Cysteine monomer has the formula:
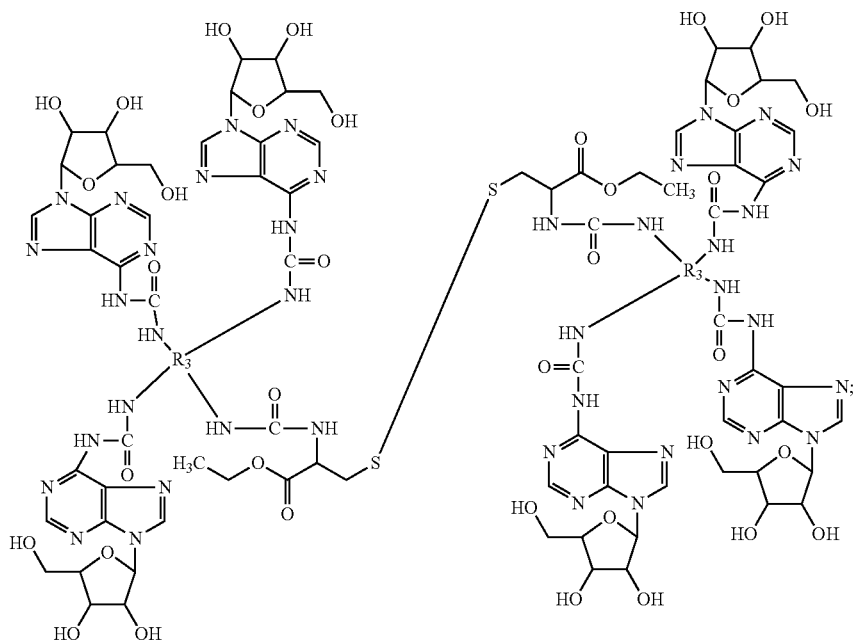
wherein $R_3$ has the formula:
and wherein each R is independently a unit having the formula:
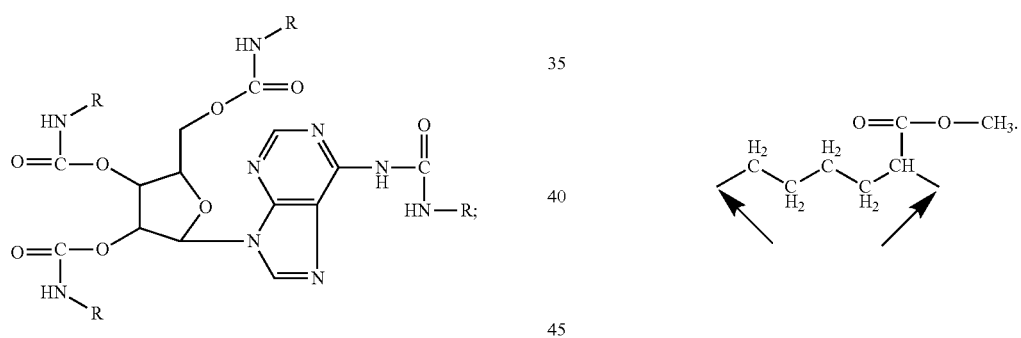
* * * * *